United States Patent
Austermann et al.

(10) Patent No.: US 12,329,364 B2
(45) Date of Patent: Jun. 17, 2025

(54) FLUID COLLECTION DEVICES INCLUDING AT LEAST ONE SHAPE MEMORY MATERIAL

(71) Applicant: PureWick Corporation, El Cajon, CA (US)

(72) Inventors: Nick Austermann, Atlanta, GA (US); Pranav Challa, Atlanta, GA (US); Young Cho, El Cajon, CA (US); Ashley Marie Johannes, Atlanta, GA (US); Andrew Meyer, Atlanta, GA (US); Eric Rehm, Lawrenceville, GA (US)

(73) Assignee: PUREWICK CORPORATION, Covington, GA (US)

( * ) Notice: Subject to any disclaimer, the term of this patent is extended or adjusted under 35 U.S.C. 154(b) by 456 days.

(21) Appl. No.: 17/597,673

(22) PCT Filed: Jul. 16, 2020

(86) PCT No.: PCT/US2020/042262
§ 371 (c)(1),
(2) Date: Jan. 18, 2022

(87) PCT Pub. No.: WO2021/016026
PCT Pub. Date: Jan. 28, 2021

(65) Prior Publication Data
US 2022/0313222 A1   Oct. 6, 2022

Related U.S. Application Data

(60) Provisional application No. 62/935,337, filed on Nov. 14, 2019, provisional application No. 62/876,500, filed on Jul. 19, 2019.

(51) Int. Cl.
A61B 10/00  (2006.01)
A61F 5/44   (2006.01)
(Continued)

(52) U.S. Cl.
CPC .......... *A61B 10/007* (2013.01); *A61F 5/4407* (2013.01); *A61F 5/453* (2013.01);
(Continued)

(58) Field of Classification Search
CPC ...... A61B 10/007; A61F 5/4407; A61F 5/453; A61F 5/455; A61F 13/84;
(Continued)

(56) References Cited

U.S. PATENT DOCUMENTS

| 670,602 A | 3/1901 | Baker |
| 737,443 A | 8/1903 | Mooers |

(Continued)

FOREIGN PATENT DOCUMENTS

| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)
(Continued)

*Primary Examiner* — Nicholas J. Weiss
*Assistant Examiner* — Gabriella E Burnette
(74) *Attorney, Agent, or Firm* — Dorsey & Whitney LLP

(57) ABSTRACT

Examples relate to systems, devices, and methods for removing fluid from a fluid collection device using a vacuum source operably coupled thereto. The fluid collection devices include urine collection devices having shape memory material that may be selectively shaped to complement the female or male anatomy near the respective urethras.

24 Claims, 22 Drawing Sheets

(51) Int. Cl.
*A61F 5/453* (2006.01)
*A61F 5/455* (2006.01)
*A61F 13/15* (2006.01)
*A61F 13/84* (2006.01)

(52) U.S. Cl.
CPC .............. *A61F 5/455* (2013.01); *A61F 13/84* (2013.01); *A61F 2013/15146* (2013.01); *A61F 2013/8494* (2013.01); *A61L 2400/16* (2013.01)

(58) Field of Classification Search
CPC .... A61F 2013/15146; A61F 2013/8494; A61F 2013/15154; A61F 5/451; A61L 2400/16
See application file for complete search history.

(56) References Cited

U.S. PATENT DOCUMENTS

| | | |
|---|---|---|
| 1,015,905 A | 1/1912 | Northrop |
| 1,032,841 A | 7/1912 | Koenig |
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,175,719 A | 3/1965 | Herndon |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | McGuire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,096,897 A | 6/1978 | Cammarata |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |

(56) References Cited

U.S. PATENT DOCUMENTS

| | | | |
|---|---|---|---|
| 4,813,943 A | 3/1989 | Smith |
| 4,820,291 A | 4/1989 | Terauchi et al. |
| 4,820,297 A | 4/1989 | Kaufman et al. |
| 4,841,728 A | 6/1989 | Jean et al. |
| 4,846,818 A | 7/1989 | Keldahl et al. |
| 4,846,819 A | 7/1989 | Welch |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-ho |
| 4,903,254 A | 2/1990 | Haas |
| 4,904,248 A | 2/1990 | Vaillancourt |
| 4,905,692 A | 3/1990 | More |
| 4,936,838 A | 6/1990 | Cross et al. |
| 4,950,262 A | 8/1990 | Takagi |
| 4,955,922 A | 9/1990 | Terauchi |
| 4,957,487 A | 9/1990 | Gerow |
| 4,965,460 A | 10/1990 | Tanaka et al. |
| 4,986,823 A | 1/1991 | Anderson et al. |
| 4,987,849 A | 1/1991 | Sherman |
| 5,002,541 A | 3/1991 | Conkling et al. |
| 5,004,463 A | 4/1991 | Nigay |
| 5,013,308 A | 5/1991 | Sullivan et al. |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | McGuire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | McGuire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,294,983 A | 3/1994 | Ersoz et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,409,475 A | 4/1995 | Steer |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,593,389 A | 1/1997 | Chang |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,735,835 A | 4/1998 | Holland |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,467,570 B1 | 10/2002 | Herold |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,551,293 B1 | 4/2003 | Mitchell |
| 6,569,133 B2 | 5/2003 | Cheng et al. |

(56) References Cited

U.S. PATENT DOCUMENTS

| | | |
|---|---|---|
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,166,092 B2 | 1/2007 | Elson et al. |
| 7,171,699 B2 | 2/2007 | Ernest et al. |
| 7,171,871 B2 | 2/2007 | Kozak |
| 7,179,951 B2 | 2/2007 | Krishnaswamy-Mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,511 B2 | 6/2009 | Marocco |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 | 12/2009 | Saadat et al. |
| 7,658,730 B2 | 2/2010 | Conley |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,343,125 B2 | 1/2013 | Kawazoe et al. |
| 8,353,074 B2 | 1/2013 | Krebs |
| 8,353,886 B2 | 1/2013 | Bester et al. |
| D676,241 S | 2/2013 | Merrill |
| 8,388,587 B1 | 3/2013 | Gmuer et al. |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,652,112 B2 | 2/2014 | Johannison et al. |
| 8,669,412 B2 | 3/2014 | Fernkvist et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |

(56) References Cited

U.S. PATENT DOCUMENTS

| | | |
|---|---|---|
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,402,424 B2 | 8/2016 | Roy |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | McGirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| 10,258,517 B1 | 4/2019 | Maschino et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,500,108 B1 | 12/2019 | Maschino et al. |
| 10,502,198 B2 | 12/2019 | Stumpf et al. |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| 10,806,642 B2 | 10/2020 | Tagomori et al. |
| D901,214 S | 11/2020 | Hu |
| 10,849,799 B2 | 12/2020 | Nishikawa et al. |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,090,183 B2 | 8/2021 | Sanchez et al. |
| 11,160,695 B2 | 11/2021 | Febo et al. |
| 11,160,697 B2 | 11/2021 | Maschino et al. |
| 11,168,420 B2 | 11/2021 | Kinugasa et al. |
| 11,179,506 B2 | 11/2021 | Barr et al. |
| 11,207,206 B2 | 12/2021 | Sharma et al. |
| 11,226,376 B2 | 1/2022 | Yamauchi et al. |
| 11,253,389 B2 | 2/2022 | Sharma et al. |
| 11,253,407 B2 | 2/2022 | Miao et al. |
| 11,326,586 B2 | 5/2022 | Milner et al. |
| 11,369,508 B2 | 6/2022 | Ecklund et al. |
| 11,369,524 B2 | 6/2022 | Hubbard et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,399,990 B2 | 8/2022 | Suyama |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| 11,839,567 B2 | 12/2023 | Davis et al. |
| D1,010,109 S | 1/2024 | Ecklund et al. |
| 11,857,716 B2 | 1/2024 | Lee et al. |
| 11,865,030 B2 | 1/2024 | Davis et al. |
| 11,890,221 B2 | 2/2024 | Ulreich et al. |
| 11,925,575 B2 | 3/2024 | Newton |
| 11,938,053 B2 | 3/2024 | Austermann et al. |
| 11,944,740 B2 | 4/2024 | Hughett et al. |
| 11,994,122 B2 | 5/2024 | Bodain |
| 11,998,475 B2 | 6/2024 | Becker et al. |
| 12,023,457 B2 | 7/2024 | Mann et al. |
| 12,042,422 B2 | 7/2024 | Davis et al. |
| D1,038,385 S | 8/2024 | Ecklund et al. |
| 12,090,083 B2 | 9/2024 | Ecklund et al. |
| 12,133,813 B2 | 11/2024 | Ulreich et al. |
| 12,138,195 B2 | 11/2024 | Alder et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0026163 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2002/0193762 A1 | 12/2002 | Suydam |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |

(56) References Cited

U.S. PATENT DOCUMENTS

| | | |
|---|---|---|
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0200936 A1 | 10/2004 | Opperthauser |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Mrginio |
| 2009/0270822 A1 | 10/2009 | Medeiros |
| 2009/0281510 A1 | 11/2009 | Fisher |
| 2009/0283982 A1 | 11/2009 | Thomas |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0210503 A1 | 8/2012 | Anzivino et al. |
| 2012/0233761 A1 | 9/2012 | Huang |

(56) References Cited

U.S. PATENT DOCUMENTS

| | | |
|---|---|---|
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0218112 A1 | 8/2013 | Thompson |
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis ...................... A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0240079 A1 | 8/2019 | Tuli |
| 2019/0247222 A1 | 8/2019 | Ecklund et al. |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |

(56) References Cited

U.S. PATENT DOCUMENTS

| | | |
|---|---|---|
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |
| 2020/0385179 A1 | 12/2020 | McCourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |

(56) References Cited

U.S. PATENT DOCUMENTS

| | | | |
|---|---|---|---|
| 2024/0148539 | A1 | 5/2024 | Austermann et al. |
| 2024/0261131 | A1 | 8/2024 | Garvey et al. |
| 2025/0009552 | A1 | 1/2025 | Blabas et al. |

FOREIGN PATENT DOCUMENTS

| | | | |
|---|---|---|---|
| CA | 2165286 | C | 9/1999 |
| CA | 2354132 | A1 | 6/2000 |
| CA | 2359091 | C | 9/2003 |
| CA | 2488867 | C | 8/2007 |
| CA | 3050918 | A1 | 8/2018 |
| CA | 3098571 | A1 | 11/2019 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1602825 | A | 4/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451693 | A | 3/2016 |
| CN | 105534632 | A | 5/2016 |
| CN | 106132360 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 102012112818 | A1 | 6/2014 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| EP | 4445881 | A2 | 10/2024 |
| EP | 4464288 | A2 | 11/2024 |
| GB | 871820 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58188016 | U | 12/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | H0626264 | U | 4/1994 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |

(56) References Cited

FOREIGN PATENT DOCUMENTS

| | | |
|---|---|---|
| JP | 2000185068 A | 7/2000 |
| JP | 2000225139 A | 8/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003038563 A | 2/2003 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |
| JP | 2005066011 A | 3/2005 |
| JP | 2005066325 A | 3/2005 |
| JP | 2005102978 A | 4/2005 |
| JP | 2005518237 A | 6/2005 |
| JP | 2005518901 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 2007259898 A | 10/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |
| JP | 2010058795 A | 3/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 2015513678 A | 5/2015 |
| JP | 3198994 B2 | 7/2015 |
| JP | 2015221390 A | 12/2015 |
| JP | 2016521191 A | 7/2016 |
| JP | 2017014698 A | 1/2017 |
| JP | 2017512603 A | 5/2017 |
| JP | 2017201272 A | 11/2017 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020520775 A | 7/2020 |
| JP | 2021007472 A | 1/2021 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20080005516 A | 1/2008 |
| KR | 20090104426 A | 10/2009 |
| KR | 20090110359 A | 10/2009 |
| KR | 20120005922 A | 1/2012 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012020506 A1 | 2/2012 |

(56) References Cited

FOREIGN PATENT DOCUMENTS

| | | |
|---|---|---|
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017001846 A1 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019050959 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021097067 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021170075 A1 | 9/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021211914 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |
| WO | 2022067392 A1 | 4/2022 |
| WO | 2022069950 A1 | 4/2022 |
| WO | 2022071429 A1 | 4/2022 |
| WO | 2022076322 A1 | 4/2022 |
| WO | 2022076427 A2 | 4/2022 |
| WO | 2022086898 A1 | 4/2022 |
| WO | 2022090199 A1 | 5/2022 |
| WO | 2022098536 A1 | 5/2022 |
| WO | 2022099087 A1 | 5/2022 |
| WO | 2022101999 A1 | 5/2022 |
| WO | 2022115692 A1 | 6/2022 |
| WO | 2022125685 A1 | 6/2022 |
| WO | 2022140545 A1 | 6/2022 |
| WO | 2022145231 A1 | 7/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |

(56) References Cited

FOREIGN PATENT DOCUMENTS

| | | | |
|---|---|---|---|
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023191764 | A1 | 10/2023 |
| WO | 2023244238 | A1 | 12/2023 |
| WO | 2024058788 | A1 | 3/2024 |
| WO | 2024253655 | A1 | 12/2024 |

OTHER PUBLICATIONS

Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 10, 2023.
Final Office Action for U.S. Appl. No. 16/433,773 mailed Oct. 25, 2022.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/662,700 mailed Sep. 30, 2022.

(56) References Cited

OTHER PUBLICATIONS

Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/IB2021/057173 mailed Nov. 5, 2021.
International Search Report and Written Opinion from International Application No. PCT/US2021/039866 mailed Oct. 7, 2021.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/018159 mailed Dec. 12, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
Issue Notification for U.S. Appl. No. 16/245,726 mailed Oct. 18, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/478,180 mailed Nov. 7, 2023.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/444,792 mailed Nov. 17, 2023.

(56) References Cited

OTHER PUBLICATIONS

Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,345 mailed Jan. 17, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 16/449,039 mailed Dec. 15, 2022.
Notice of Allowance for U.S. Appl. No. 16/899,956 mailed Dec. 1, 2022.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 15/384,196, filed Dec. 19, 2016.
U.S. Appl. No. 17/451,719, filed Oct. 19, 2021.
U.S. Appl. No. 17/664,487, filed May 23, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.

(56) References Cited

OTHER PUBLICATIONS

U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 62/923,279, filed Oct. 18, 2019.
U.S. Appl. No. 62/926,767, filed Oct. 28, 2019.
U.S. Appl. No. 62/967,158, filed Jan. 26, 2020.
U.S. Appl. No. 62/991,754, filed Mar. 19, 2020.
U.S. Appl. No. 63/008,112, filed Apr. 10, 2020.
U.S. Appl. No. 63/094,646, filed Oct. 21, 2020.
U.S. Appl. No. 63/150,640, filed Feb. 18, 2021.
U.S. Appl. No. 63/191,558, filed May 21, 2021.
U.S. Appl. No. 63/192,289, filed May 24, 2021.
U.S. Appl. No. 63/208,262, filed Jun. 8, 2021.
U.S. Appl. No. 63/230,897, filed Aug. 9, 2021.
U.S. Appl. No. 63/241,328, filed Sep. 7, 2021.
U.S. Appl. No. 63/308,190, filed Feb. 9, 2022.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers. com/textile-resources/synthetic-fibers/polypropylene-fiber/ polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas,"A Solution For An Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article,"Zylinder (Geometrie)", https://de.wikipedia.org/w/index.php?title=Zylinder_(Geometrie)&oldid=154862081, version of Jun. 1, 2016, 7 pages.
Advisory Action for U.S. Appl. No. 16/904,868 mailed Jun. 15, 2022.
Advisory Action for U.S. Appl. No. 16/905,400 mailed Feb. 16, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/904,868 mailed Mar. 10, 2022.
International Search Report and Written Opinion from International Application No. PCT/US2020/057562 mailed Jan. 27, 2021.
International Search Report and Written Opinion from International Application No. PCT/US2021/026607 mailed Jul. 29, 2021.
International Search Report and Written Opinion from International Application No. PCT/US2021/045188 mailed Jan. 26, 2022.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/015471 mailed May 16, 2022.

(56) References Cited

OTHER PUBLICATIONS

International Search Report and Written Opinion from International Application No. PCT/US2022/016942 mailed Jun. 8, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/905,400 mailed Apr. 27, 2022.
Non-Final Office Action for U.S. Appl. No. 17/662,700 mailed Jul. 22, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/905,400 mailed Aug. 17, 2022.
Notice of Allowance for U.S. Appl. No. 17/088,272 mailed Mar. 4, 2022.
Notice of Allowance for U.S. Appl. No. 17/330,657 mailed Mar. 16, 2022.
Notice of Allowance for U.S. Appl. No. 29/741,751 mailed Jun. 9, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.

(56) References Cited

OTHER PUBLICATIONS

International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/048211 mailed Dec. 22, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
International Search Report and Written Opinion from International Application No. PCT/US2021/047536 mailed Dec. 23, 2021.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/899,956 mailed Dec. 29, 2021.
Notice of Allowance for U.S. Appl. No. 17/088,272 mailed Aug. 5, 2021.
Notice of Allowance for U.S. Appl. No. 17/088,272 mailed Nov. 24, 2021.
Notice of Allowance for U.S. Appl. No. 17/330,657 mailed Nov. 26, 2021.

(56) References Cited

OTHER PUBLICATIONS

Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 14/433,773, filed Apr. 3, 2020.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/614,173, filed Nov. 24, 2021.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.

(56) References Cited

OTHER PUBLICATIONS

U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC v. Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.

"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, Aug. 30, 2017, 4 pages.
"Underwear that absorbs your period", Thinx!, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical. com, 6 pages.
MaCaulay, et al., "A Noninvasive Continence Management System: Development and Evaluation of a Novel Toileting Device for Women", The Wound, Ostomy and Continence Nurses Society, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
PureWick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
Corrected Notice of Allowability for U.S. Appl. No. 17/330,657 mailed Dec. 9, 2021.
Final Office Action for U.S. Appl. No. 16/905,400 mailed Dec. 9, 2021.
Non-Final Office Action for U.S. Appl. No. 16/245,726 mailed Jan. 21, 2022.
Non-Final Office Action for U.S. Appl. No. 29/741,751 mailed Jan. 18, 2022.
Restriction Requirement for U.S. Appl. No. 16/433,773 mailed Dec. 7, 2021.
U.S. Appl. No. 17/394,055, filed Aug. 4, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/655,464, filed Mar. 18, 2022.
U.S. Appl. No. 62/935,337, filed Nov. 14, 2019.
U.S. Appl. No. 62/967,977, filed Jan. 30, 2020.
U.S. Appl. No. 63/133,892, filed Jan. 5, 2021.
U.S. Appl. No. 63/138,878, filed Jan. 19, 2021.
U.S. Appl. No. 63/299,208, filed Jan. 13, 2022.
"Rising Warrior Insulated Gallon Jug Cover", https://www.amazon.com/Rising-Warrior-Insulated-Sleeve, 2021, 2 pages.

(56) References Cited

OTHER PUBLICATIONS

"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Tsipenyuk, et al., "Use of biomimetic hexagonal surface texture in friction against lubricated skin", Journal of The Royal Society—Interface, 2014, pp. 1-6.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 17/444,792 mailed Apr. 3, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 17/051,550 mailed Mar. 13, 2024.
Issue Notification for U.S. Appl. No. 17/051,554 mailed Mar. 6, 2024.
Non-Final Office Action for U.S. Appl. No. 16/904,868 mailed Mar. 12, 2024.
Non-Final Office Action for U.S. Appl. No. 17/450,864 mailed May 29, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 18/003,029 mailed Mar. 26, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/449,039 mailed Mar. 28, 2024.
Notice of Allowance for U.S. Appl. No. 17/326,980 mailed Apr. 5, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/667,097 mailed Mar. 20, 2024.
U.S. Appl. No. 17/444,792, filed Aug. 10, 2021.
U.S. Appl. No. 18/249,577, filed Oct. 19, 2021.
U.S. Appl. No. 18/610,523, filed Mar. 20, 2024.
U.S. Appl. No. 18/662,216, filed May 13, 2024.
U.S. Appl. No. 18/693,638, filed Mar. 20, 2024.
U.S. Appl. No. 18/694,090, filed Mar. 21, 2024.
U.S. Appl. No. 63/561,893, filed Dec. 11, 2023.

(56) References Cited

OTHER PUBLICATIONS

Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org/web/20200309194847/https://en.wikipedia.org/wiki/Fiberglass last accessed Mar. 11, 2024.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/451,345 mailed Jul. 3, 2024.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/164,800 mailed Jan. 8, 2025.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/164,800 mailed Oct. 22, 2024.
Final Office Acton for U.S. Appl. No. 17/595,747 mailed Dec. 12, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/663,330 mailed Jul. 1, 2024.
Non-Final Office Action for U.S. Appl. No. 17/664,487 mailed Jun. 17, 2024.

(56) References Cited

OTHER PUBLICATIONS

Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/450,864 mailed Sep. 18, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
U.S. Appl. No. 17/013,822, filed Sep. 7, 2020.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63,564,696, filed Mar. 13, 2024.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, Abut Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Final Office Action for U.S. Appl. No. 17/451,345 mailed Feb. 6, 2025.
Final Office Action for U.S. Appl. No. 17/653,314 mailed Jan. 30, 2025.
International Search Report and Written Opinion from International Application No. PCT/US2024/053681 mailed Jan. 27, 2025.
Issue Notification for U.S. Appl. No. 17/661,090 mailed Feb. 5, 2025.
Issue Notification for U.S. Appl. No. 18/140,751 mailed Feb. 12, 2025.
Non-Final Office Action for U.S. Appl. No. 17/653,137 mailed Jan. 28, 2025.
Notice of Allowance for U.S. Appl. No. 16/904,868 mailed Jan. 21, 2025.
Notice of Allowance for U.S. Appl. No. 17/596,629 mailed Jan. 29, 2025.
Notice of Allowance for U.S. Appl. No. 17/749,340 mailed Feb. 14, 2025.

(56) References Cited

OTHER PUBLICATIONS

U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/103,165, filed Feb. 11, 2025.
U.S. Appl. No. 63/181,709, filed Apr. 29, 2021.

* cited by examiner

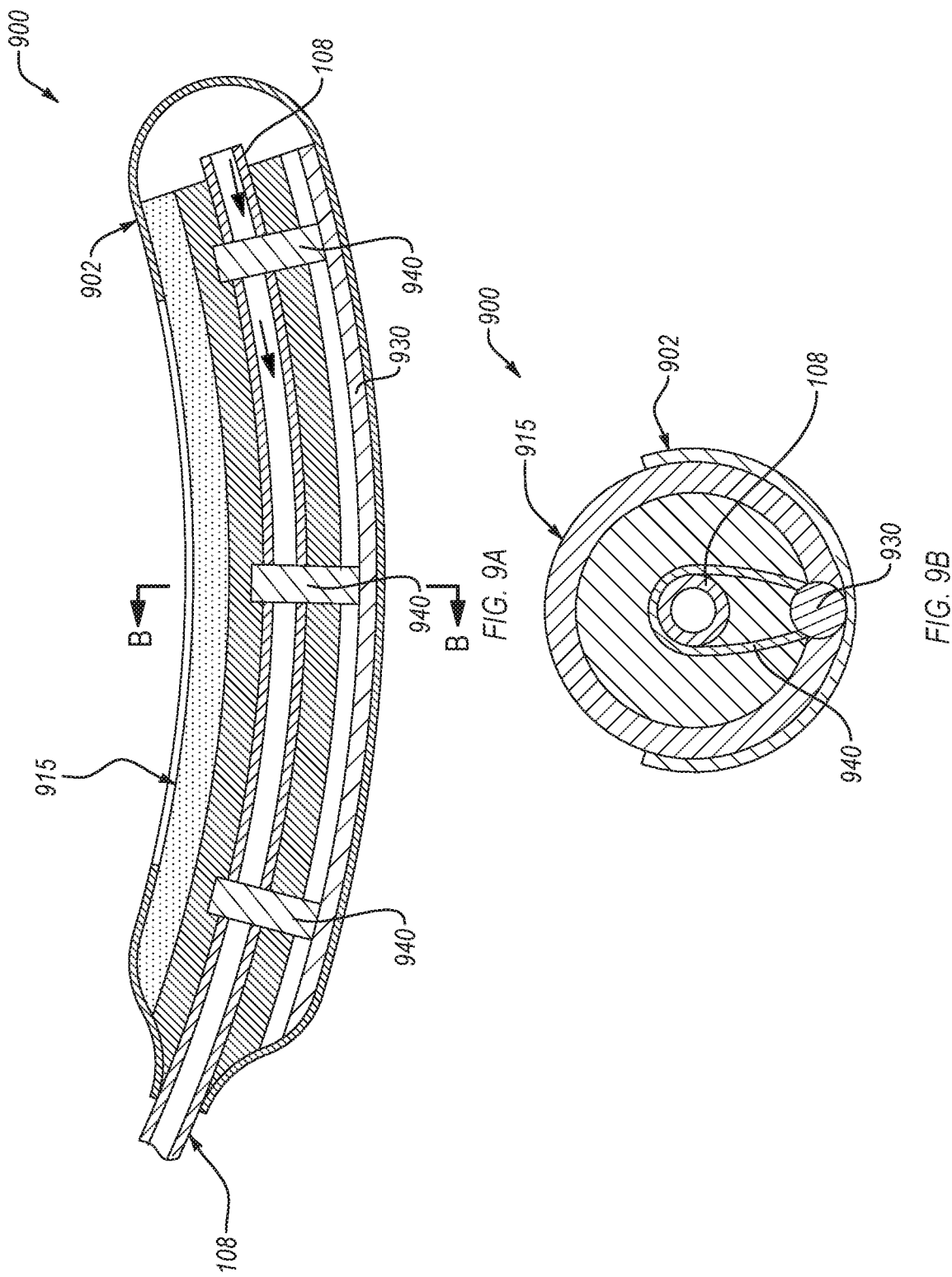

```
                                                            ┌─1700
                                                           ╱
                                                          ╱

┌─────────────────────────────────────────────────────────────────────┐
│  Positioning an opening of a fluid collection device adjacent to    │
│  a female urethra or around a male urethra, the fluid collection    │
│  device including: a fluid impermeable barrier at least partially   │
│  defining a chamber, the fluid impermeable barrier also defining    │
│  an opening extending therethrough, the opening configured to be    │─1710
│  positioned adjacent to the female urethra or have the male         │
│  urethra positioned there through; a porous material disposed in    │
│  the chamber; and a shape memory material incorporated in the       │
│  fluid collection device, the shape memory material being sized,    │
│  shaped, and positioned to retain a selected geometric configuration│
└─────────────────────────────────────────────────────────────────────┘
                                    │
                                    ▼
┌─────────────────────────────────────────────────────────────────────┐
│  Shaping the fluid collection device into the selected geometric    │
│  configuration, wherein the selected geometric configuration is     │─1720
│  complementary to contours of anatomy of a wearer in a region       │
│  proximate to the female urethra or the male urethra of the wearer  │
└─────────────────────────────────────────────────────────────────────┘
                                    │
                                    ▼
┌─────────────────────────────────────────────────────────────────────┐
│  Receiving fluid from the female urethra or the male urethra into   │─1730
│  a chamber of the fluid collection device                           │
└─────────────────────────────────────────────────────────────────────┘
```

*FIG. 17*

FLUID COLLECTION DEVICES INCLUDING AT LEAST ONE SHAPE MEMORY MATERIAL

CROSS-REFERENCE TO RELATED APPLICATIONS

This application is a U.S. Nationalization of PCT International Application No. PCT/US2020/042262 filed on Jul. 16, 2020, which claims priority to U.S. Provisional Application No. 62/876,500 filed on Jul. 19, 2019 and U.S. Provisional Application No. 62/935,337 filed on Nov. 14, 2019, the disclosure of each of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections.

Thus, users and manufacturers of fluid collection devices continue to seek new and improved devices, systems, and methods to collect urine.

SUMMARY

Embodiments disclosed herein are related to devices, systems, and methods of using fluid collection devices having shape memory material therein. In an embodiment, a fluid collection device is disclosed. The fluid collection device includes a fluid impermeable barrier at least partially defining a chamber, the fluid impermeable barrier also defining an opening extending therethrough, the opening configured to be positioned adjacent to a female urethra or have a male urethra positioned therethrough. The fluid collection device includes a porous material disposed in the chamber. The fluid collection device includes a shape memory material incorporated in the fluid collection device. The shape memory material is sized, shaped, and positioned to retain a selected geometric configuration.

In an embodiment, a fluid collection system is disclosed. The fluid collection system includes a fluid storage container configured to hold a fluid. The fluid collection system includes a fluid collection device fluidly coupled to the fluid storage container. The fluid collection device includes a fluid impermeable barrier at least partially defining a chamber, the fluid impermeable barrier also defining an opening extending therethrough, the opening configured to be positioned adjacent to a female urethra or have a male urethra positioned therethrough. The fluid collection device includes a porous material disposed in the chamber. The fluid collection device includes a shape memory material incorporated in the fluid collection device. The shape memory material is sized, shaped, and positioned to retain a selected geometric configuration. The fluid collection device includes a conduit including an inlet and an outlet, the outlet being fluidly coupled to the fluid storage container and the inlet being positioned in a portion of the chamber selected to be at a gravimetrically low point of the fluid collection device when worn. The fluid collection system includes a vacuum source fluidly coupled to one or more of the fluid storage container or the fluid collection device via the conduit, the vacuum source configured to draw fluid from the fluid collection device via the conduit.

In an embodiment, a method to collect fluid is disclosed. The method includes positioning an opening of a fluid collection device adjacent to a female urethra or around a male urethra. The fluid collection device includes a fluid impermeable barrier at least partially defining a chamber, the fluid impermeable barrier also defining an opening extending therethrough, the opening configured to be positioned adjacent to the female urethra or have the male urethra positioned therethrough. The fluid collection device includes a porous material disposed in the chamber. The fluid collection device includes a shape memory material incorporated in the fluid collection device. The shape memory material is sized, shaped, and positioned to retain a selected geometric configuration. The method includes shaping the fluid collection device into the selected geometric configuration. The selected geometric configuration is complementary to contours of anatomy of a wearer in a region proximate to the female urethra or the male urethra of the wearer. The method includes receiving fluid from the female urethra or the male urethra into a chamber of the fluid collection device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 9A is a cross-sectional view of a fluid collection device, according to an embodiment.

FIG. 9B is a cross-sectional view of the fluid collection device taken along plane B-B of FIG. 9A, according to an embodiment.

FIG. 17 is a flow diagram of a method to collect fluid, according to an embodiment.

DETAILED DESCRIPTION

Embodiments disclosed herein are related to devices, systems, and methods of using fluid collection devices and systems. The devices, systems, and methods of using fluid collection devices and systems include at least one shape memory material for forming and maintaining the fluid collection device into a selected shape. The shape memory material may enable for selective manipulation of the fluid collection device to contour to the anatomical features of variously sized wearers.

The fluid collection devices disclosed herein include a fluid impermeable barrier that at least partially defines a chamber. The fluid impermeable barrier also defines an opening extending therethrough that is configured to be positioned adjacent to a female urethra or have a male urethra positioned therethrough. The fluid collection devices disclosed herein may include a porous material disposed in the chamber. The fluid collection devices disclosed herein include shape memory material carried by one or more components thereof, such as the fluid impermeable barrier, the porous material, or another component. The fluid collection devices also include a conduit having a channel extending between an inlet and outlet thereof. The inlet is configured to be coupled to a suction source and the outlet is configured to be fluidly coupled to a fluid storage (vessel or container).

The fluid collection devices disclosed herein are configured to collect fluid(s) from a wearer. The shape of the fluid collection device may be manipulated and at least temporarily maintained in a selected shape to provide a more comfortable and effective fit on the wearer. By shaping the fluid collection device with the shape memory material to match the anatomical shape of the wearer, more of the fluid may be collected and retained in the fluid collection device. For example, shaping the fluid collection device to match the anatomical shape of the wearer inhibits the fluid collection device from moving away from the groin of the wearer (e.g., when the wearer moves). Moving the fluid collection device away from the wearer increases the likelihood that fluid leaks from the fluid collection device during use. As such, shaping the fluid collection device with the shape memory material to match the anatomical shape of the wear minimizes leaks.

The fluid collected by the fluid collection devices may include urine. The fluid(s) collected by the fluid collection devices may also include at least one of vaginal discharge, penile discharge, reproductive fluids, blood, sweat, or other bodily fluids. The fluid collection devices disclosed herein are configured to be used in fluid collection systems, which apply suction in the chamber to remove the fluid from the fluid collection device.

Figure 1A:
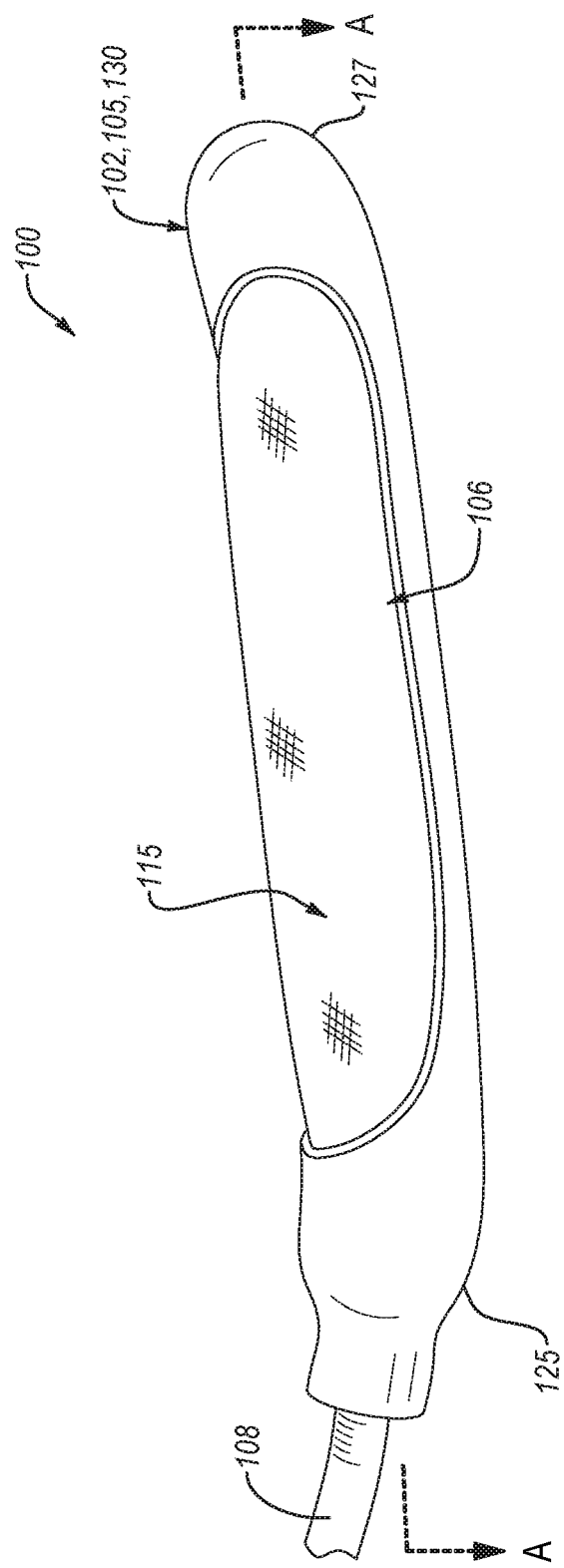
FIG. 1A is an isometric view of a fluid collection device, according to an embodiment.
Figure 1B:
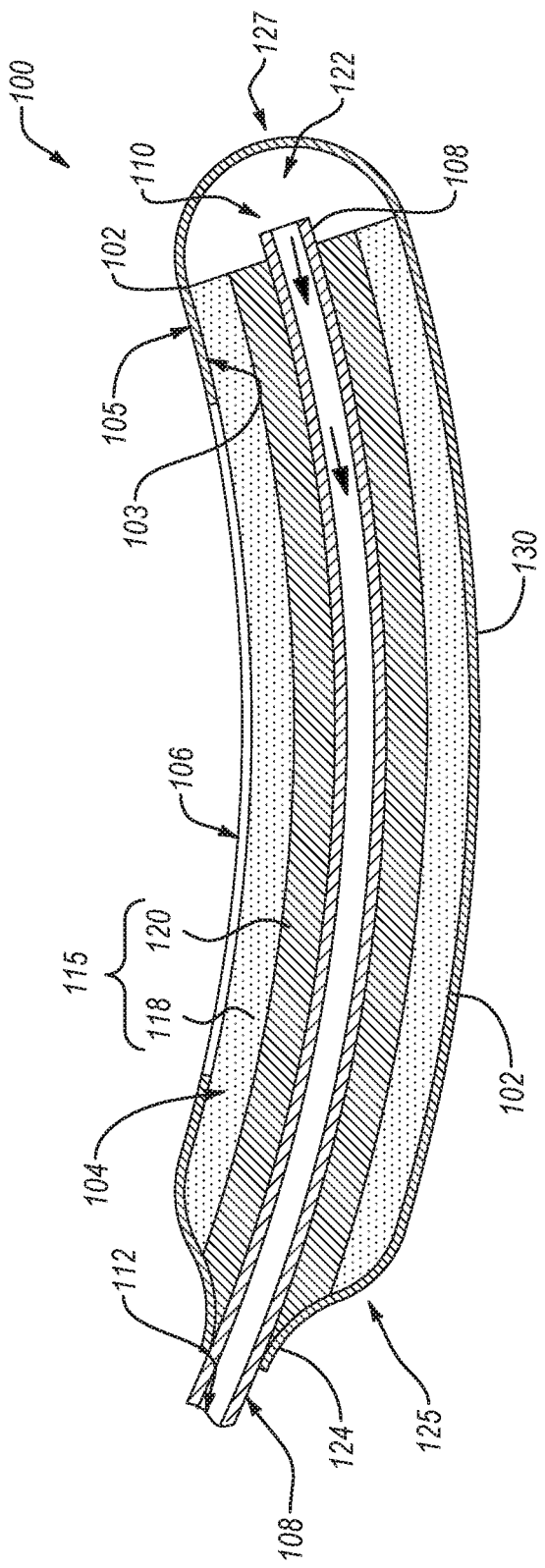
FIG. 1B is cross-sectional view of the fluid collection device taken along the plane A-A of FIG. 1A, according to an embodiment.

FIG. 1A is an isometric view of a fluid collection device 100, according to an embodiment. FIG. 1B is cross-sectional view of the fluid collection device 100 taken along the plane A-A of FIG. 1A, according to an embodiment. The fluid collection device 100 is an example of a female fluid collection device for receiving and collecting fluid(s) from a female. The fluid collection device 100 includes a fluid impermeable barrier 102, porous material 115 (e.g., wicking material) disposed in a chamber within the fluid impermeable barrier 102, at least one shape memory material 130, and an optional conduit 108 at least partially disposed within the chamber.

The fluid impermeable barrier 102 at least partially defines a chamber 104 (e.g., interior region) and an opening 106. For example, the interior surface(s) 103 of the fluid impermeable barrier 102 at least partially defines the chamber 104 within the fluid collection device 100. The fluid impermeable barrier 102 temporarily stores the fluid(s) in the chamber 104. The fluid impermeable barrier 102 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 102 substantially prevents the fluid(s) from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least one or more portions of at least an outer surface 105 of the fluid impermeable barrier 102 may be formed from a soft and/or smooth material, thereby reducing chaffing.

In some examples, the fluid impermeable barrier 102 may be tubular (ignoring the opening), such as substantially cylindrical (as shown), oblong, prismatic, or flattened tubes. During use, the outer surface 105 of the fluid impermeable barrier 102 may contact the wearer. The fluid impermeable barrier 102 may be sized and shaped to fit in the gluteal cleft between the legs of a female wearer.

The opening 106 provides an ingress route for fluids to enter the chamber 104. The opening 106 may be defined by the fluid impermeable barrier 102 such as by an inner edge of the fluid impermeable barrier 102. For example, the opening 106 is formed in and extends through the fluid impermeable barrier 102, from the outer surface 105 to the inner surface 103, thereby enabling fluid(s) to enter the chamber 104 from outside of the fluid collection device 100. The opening 106 may be an elongated hole in the fluid impermeable barrier 102. For example, the opening 106 may be defined as a cut-out in the fluid impermeable barrier 102. The opening 106 may be located and shaped to be positioned adjacent to a female urethra.

The fluid collection device 100 may be positioned proximate to the female urethra and urine may enter the chamber of the fluid collection device 100 via the opening 106. The fluid collection device 100 is configured to receive the fluid(s) into the chamber 104 via the opening 106. When in use, the opening 106 may have an elongated shape that extends from a first location below the urethral opening (e.g., at or near the anus or the vaginal opening) to a second location above the urethral opening (e.g., at or near the top of the vaginal opening or the pubic hair).

The opening 106 may have an elongated shape because the space between the legs of a female is relatively small when the legs of the female are closed, thereby only permitting the flow of the fluid(s) along a path that corresponds to the elongated shape of the opening 106 (e.g., longitudinally extending opening). The opening 106 in the fluid impermeable barrier 102 may exhibit a length that is measured along the longitudinal axis of the fluid collection device 100 that may be at least about 10% of the length of the fluid collection device 100, such as about 25% to about 50%, about 40% to about 60%, about 50% to about 75%, about 65% to about 85%, or about 75% to about 95% of the length of the fluid collection device 100.

The opening 106 in the fluid impermeable barrier 102 may exhibit a width that is measured transverse to the longitudinal axis of the fluid collection device 100 that may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 may exhibit a width that is greater than 50% of the circumference of the fluid collection device 100 since the vacuum (e.g., suction) through the conduit 108 pulls the fluid through the porous material 115 and into the conduit 108. In some examples, the opening 106 may be vertically oriented (e.g., having a major axis parallel to the longitudinal axis of the device 100). In some examples (not shown), the opening 106 may be horizontally oriented (e.g., having a major axis perpendicular to the longitudinal axis of the device 100). In an example, the fluid impermeable barrier 102 may be configured to be attached to the wearer, such as adhesively attached (e.g., with a hydrogel adhesive) to the wearer. According to an example, a suitable adhesive is a hydrogel layer.

In some examples, the fluid impermeable barrier 102 may define an aperture 124 sized to receive the conduit 108. The at least one conduit 108 may be disposed in the chamber 104 via the aperture 124. The aperture 124 may be sized and shaped to form an at least substantially fluid tight seal against the conduit 108 or the at least one tube thereby substantially preventing the fluid(s) from escaping the chamber 104.

The fluid impermeable barrier 102 may include markings (not shown) thereon, such as one or more markings to aid a wearer in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

The fluid collection device 100 includes porous material 115 disposed in the chamber 104. The porous material 115 may cover at least a portion (e.g., all) of the opening 106. The porous material 115 is exposed to the environment outside of the chamber 104 through the opening 106. The porous material 115 may be configured to move any fluid away from the opening 106, thereby preventing the fluid from escaping the chamber 104. The permeable properties referred to herein may be wicking, capillary action, diffusion, or other similar properties or processes, and are referred to herein as "permeable" and/or "wicking." Such "wicking" may not include absorption of fluid into the porous material. Put another way, substantially no absorption of fluid into the material may take place after the material is exposed to the fluid and removed from the fluid for a time. While no absorption is desired, the term "substantially no absorption" may allow for nominal amounts of absorption of fluid into the porous material (e.g., absorbency), such as less than about 10 wt % of the dry weight of the porous material, less than about 7 wt %, less than about 5 wt %, less than about 3 wt %, less than about 2 wt %, less than about 1 wt %, or less than about 0.5 wt % of the dry weight of the porous material. The porous material 115 may also wick the fluid generally towards an interior of the chamber 104, as discussed in more detail below. The porous material 115 may include one or more of a fluid permeable membrane 118 or a fluid permeable support 120. However, in some embodiments, it is noted that the porous material 115 may include an absorption material (e.g., hydrophilic material) instead of a wicking material.

The fluid collection device 100 may include the fluid permeable membrane 118 disposed in the chamber 104. The fluid permeable membrane 118 may cover at least a portion (e.g., all) of the opening 106. The fluid permeable membrane 118 may be composed to wick fluid away from the opening 106, thereby preventing the fluid from escaping the chamber 104.

The fluid permeable membrane 118 may include any material that may wick the fluid. For example, the fluid permeable membrane 118 may include fabric, such as a gauze (e.g., a silk, linen, or cotton gauze), another soft fabric, or another smooth fabric. Forming the fluid permeable membrane 118 from gauze, soft fabric, and/or smooth fabric may reduce chaffing caused by the fluid collection device 100.

The fluid collection device 100 may include the fluid permeable support 120 disposed in the chamber 104. The fluid permeable support 120 is configured to support the fluid permeable membrane 118 since the fluid permeable membrane 118 may be formed from a relatively foldable, flimsy, or otherwise easily deformable material. For example, the fluid permeable support 120 may be positioned such that the fluid permeable membrane 118 is disposed between the fluid permeable support 120 and the fluid impermeable barrier 102. As such, the fluid permeable support 120 may support and maintain the position of the fluid permeable membrane 118. The fluid permeable support 120 may include any material that may wick the fluid, such as any of the fluid permeable membrane materials disclosed herein above. For example, the fluid permeable membrane material(s) may be utilized in a more dense or rigid form than in the fluid permeable membrane 118 when used as the fluid permeable support 120. The fluid permeable support 120 may be formed from any fluid permeable material that is less deformable than the fluid permeable membrane 118. For example, the fluid permeable support 120 may include a porous polymer (e.g., nylon, polyester, polyurethane, polyethylene, polypropylene, etc.) structure or an open cell foam. In some examples, the fluid permeable support 120 may be formed from a natural material, such as cotton, wool, silk, or combinations thereof. In such examples, the material may have a coating to prevent or limit absorption of fluid into the material, such as a water repellent coating. In some examples, the fluid permeable support 120 may be formed from fabric, felt, gauze, or combinations thereof. In some examples, the fluid permeable membrane 118 may be optional. For example, the porous material 115 may include only the fluid permeable support 120. In some examples, the fluid permeable support 120 may be optionally omitted from the fluid collection device 100. For example, the porous material 115 may only include the fluid permeable membrane 118.

The fluid permeable support 120 may have a greater ability to wick fluids than the fluid permeable membrane 118, such as to move the fluid inwardly from the outer surface of the fluid collection device 100. In some examples, the wicking ability of the fluid permeable support 120 and the fluid permeable membrane 118 may be substantially the same.

The fluid permeable membrane 118 and the fluid permeable support 120 may at least substantially completely fill the portions of the chamber 104 that are not occupied by the conduit 108. In some examples, the fluid permeable membrane 118 and the fluid permeable support 120 may not substantially completely fill the portions of the chamber 104 that are not occupied by the conduit 108. In such an example, the fluid collection device 100 includes the reservoir 122 (FIG. 1B) disposed in the chamber 104.

The reservoir 122 is a substantially unoccupied portion of the chamber 104. The reservoir 122 may be defined between the fluid impermeable barrier 102 and one or both of the fluid permeable membrane 118 and fluid permeable support 120. The fluid(s) that are in the chamber 104 may flow through the fluid permeable membrane 118 and/or fluid permeable support 120 to the reservoir 122. The reservoir 122 may retain of the fluid(s) therein.

The fluid(s) that are in the chamber 104 may flow through the fluid permeable membrane 118 and/or fluid permeable support 120 to the reservoir 122. The fluid impermeable barrier 102 may retain the fluid(s) in the reservoir 122. While depicted in the second end region 127, the reservoir 122 may be located in any portion of the chamber 104 such as the first end region 125. The reservoir 122 may be located in a portion of the chamber 104 that is designed to be located in a gravimetrically low point of the fluid collection device when the device is worn.

In some examples (not shown), the fluid collection device 100 may include multiple reservoirs, such as a first reservoir that is located at the portion of the chamber 104 closest to the inlet 110 (e.g., second end region 127) and a second reservoir that is located at the portion of the of the chamber 104 that is closest to the outlet 112 of the conduit 108 (e.g., first end region 125). In another example, the fluid permeable support 120 is spaced from at least a portion of the conduit, and the reservoir 122 may be the space between the fluid permeable support 120 and the conduit.

The conduit 108 may be at least partially disposed in the chamber 104. The conduit 108 may be used to remove fluid form the chamber 104. The conduit 108 (e.g., a tube) includes an inlet 110 and an outlet 112 positioned downstream from the inlet 110. The outlet 112 may be operably coupled to a suction source, such as a vacuum pump for withdrawing fluid form the chamber through the conduit 108. For example, the conduit 108 may extend into the fluid impermeable barrier 102 from the first end region 125 and may extend to the second end region 127 to a point proximate to the reservoir 122 therein such that the inlet 110 is in fluid communication with the reservoir 122. The conduit 108 fluidly couples the chamber 104 with the fluid storage container (not shown) or the vacuum source (not shown).

The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 108 may include silicon or latex. In some examples, the conduit 108 may include one or more portions that are resilient, such as to by having one or more of a diameter or wall thickness that allows the conduit to be flexible.

As shown in FIG. 1B, the end of the conduit 108 may extend through a bore in the fluid permeable membrane 118 and/or fluid permeable support 120, such as into the reservoir 122. For example, the inlet 110 may be extend into or be positioned in the reservoir 122. In the illustrated embodiment, the conduit 108 is at least partially disposed in the reservoir 122. In some examples (not shown), the conduit 108 may enter the chamber 104 in the second end region and the inlet 110 of the conduit 108 may be disposed in the second end region (e.g., in the reservoir 122). The fluid collected in the fluid collection device 100 may be removed from the chamber 104 via the conduit 108.

In some examples, the inlet 110 may not extend into the reservoir 122. In such examples, the inlet 110 may be disposed within the porous material 115 (fluid permeable membrane 118 and/or fluid permeable support 120) or at a terminal end thereof. For example, an end of the conduit 108 may be coextensive with or recessed within the fluid permeable membrane 118 and/or fluid permeable support 120.

Locating the inlet 110 at or near a location expected to be the gravimetrically low point of the chamber 104 when worn by a wearer enables the conduit 108 to receive more of the fluid(s) than if inlet 110 was located elsewhere and reduce the likelihood of pooling (e.g., pooling of the fluid(s) may cause microbe growth and foul odors). For instance, the fluid(s) in the fluid permeable membrane 118 and the fluid permeable support 120 may flow in any direction due to capillary forces. However, the fluid(s) may exhibit a preference to flow in the direction of gravity, especially when at least a portion of the fluid permeable membrane 118 and/or the fluid permeable support 120 is saturated with the fluid(s). Accordingly, one or more of the inlet 110 or the reservoir 122 may be located in the fluid collection device in a position expected to be the gravimetrically low point in the fluid collection device when worn by a wearer, such as the second end region 127.

In an example, the conduit 108 is configured to be at least insertable into the chamber 104. In such an example, the conduit 108 may include one or more markers (not shown) on an exterior thereof that are located to facilitate insertion of the conduit 108 into the chamber 104. For example, the conduit 108 may include one or more markings thereon that are configured to prevent over or under insertion of the conduit 108, such as when the conduit 108 defines an inlet 110 that is configured to be disposed in or adjacent to the reservoir 122. In another example, the conduit 108 may include one or more markings thereon that are configured to facilitate correct rotation of the conduit 108 relative to the chamber 104. The one or more markings may include a line, a dot, a sticker, or any other suitable marking.

As described in more detail below, the conduit 108 is configured to be coupled to, and at least partially extend between, one or more of the fluid storage container (not shown) and the vacuum source (not shown). In an example, the conduit 108 is configured to be directly connected to the vacuum source (not shown). In such an example, the conduit 108 may extend from the fluid impermeable barrier 102 by at least one foot, at least two feet, at least three feet, or at least six feet. In another example, the conduit 108 is configured to be indirectly connected to at least one of the fluid storage container (not shown) and the vacuum source (not shown). In some examples, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 are configured to fluidly couple (e.g., directly or indirectly) the vacuum source (not shown) to the chamber 104 (e.g., the reservoir 122). As the vacuum source (FIG. 16) applies a vacuum/suction in the conduit 108, the fluid(s) in the chamber 104 (e.g., at the second end region such as in the reservoir 122) may be drawn into the inlet 110 and out of the fluid collection device 100 via the conduit 108. In some examples, the conduit may be frosted or opaque (e.g., black) to obscure visibility of the fluid(s) therein.

The fluid collection device 100 includes a shape memory material 130. The shape memory material may be sized, shaped, and positioned in the fluid collection device to cause at least a portion of the fluid collection device 100 to retain a selected shape (e.g., geometric configuration). In an embodiment, the shape memory material 130 is configured to be bent, shaped, or otherwise deformed (hereafter collectively referred to as "shape," "shaped," or "shaping"). In an example, the shape memory material 130 is configured to be shaped along an entire length thereof. Allowing the shape memory material 130 to be shaped along the entire length thereof may allow the fluid collection device 100 to exhibit a shape that substantially corresponds to the anatomical features of the wearer. In an example, the shape memory material 130 is configured to be shaped at one or more selected location thereof. In such an example, the selected locations of the shape memory material 130 may be preferentially shaped relative to the rest of the shape memory material 130. While configuring the shape memory material 130 to be shaped at the selected location may inhibit the fluid collection device 100 from exhibiting a shape that substantially corresponds to the anatomical features of the wearer, it may facilitate shaping of the fluid collection device 100, especially for less experienced wearers. In an embodiment, the shape memory material may not be configured to be shaped. Instead, the shape memory material may exhibit a selected shape that corresponds or substantially corresponds to the anatomical feature of the wearer. In such an embodiment, the shape memory material 130 may be more rigid and/or resilient than the rest of the fluid collection device 100 thereby causing at least a portion of the fluid collection device 100 to correspond to the selected shape of the shape memory material 130.

The shape memory material 130 may include a shape memory polymer or a metal (e.g., shape memory metal). Generally, the shape memory materials are composed to adopt an intermediate or permanent shape in response to a stimuli. The stimuli may include an external physical force (e.g., bending force), heat, electrical bias, or a magnetic field. While the term "shape memory" is used to describe some of the "shape memory materials" herein, it should be understood that, in some examples, the material modified by the term "shape memory" may not necessarily need to return to a preselected shape upon application of a stimuli, as understood as the classical definition of the "shape memory material." Rather, at least some of the shape memory materials herein may simply hold a selected shape when bent, set, or cured into a specific shape and/or when cooled in a specific shape, regardless of the stimuli applied thereto after. The shape memory materials may be returned to the original shape or changed to a new shape by application of stimuli. For example, a metal wire bent to a first shape may be utilized as the shape memory material, whereinafter the metal wire may be modified to a second shape via physical force applied thereto or via heating. However, in some embodiments, the shape memory materials may exhibit a selected shape, as discussed above and application of the stimuli may cause the shape memory material to deform (e.g., elastically deform or bend) into an intermediate shape. In such embodiments, the shape memory material may return to the initial shape upon removal of the stimuli such that the shape memory material does not maintain the intermediate shape.

In an embodiment, the shape memory material may include metal, such as an elemental metal, an alloy, or shape memory alloy. Suitable shape memory metals may include standard steels, stainless steel, carbon alloy steel, head treated steel, aluminum, silver, copper, iron, nickel, zinc, tin, beryllium, or the like. Suitable shape memory alloys may include stainless steel; galvanized steel; aluminum alloys; nickel-titanium alloys, such as Nitinol, Ni—Ti—Cu, Ni—Ti, Co, or the like; copper-based alloys such as Cu—Zn—Al, Cu—Al—Ni, Cu—Al—Sn, or the like; Co—Cr—Ni—Mo alloys (e.g., Elgiloy®) or the like; or any other alloy having shape memory characteristics. As explained above, the shape memory metals or alloys may merely be metals or alloys that may be shaped to a selected configuration. In some examples, the shape memory metals or alloys may return to a primary shape when an external stimuli is applied thereto. In some examples, the outer surface of the shape memory metal may be coated with a polymer, anodized, passivated, or otherwise treated to prevent corrosion.

Shape memory polymers ("SMPs") may include polyurethane-based SMPs such as a copolymer (e.g., copolyester, polyurethane, polyetherester, etc.) including blocks of one or more of poly(ε-caprolactone), polyethyleneterephthalate (PET), polyethyleneoxide (PEO), polyethylene glycol (PEG), polystyrene, polymethylmethacrylate (PMMA), Polybutylmethacrylate (PBMA), poly(N,N-butadiene), poly(N-methyl-N-oxazoline), polytetrahydrofuran, or poly(butylene terephthalate); thermoplastic polymers such as polyether ether ketone (PEEK), nylon, acetal, polytetrafluoroethylene (PTFE), polypropylene, polyethylene, acrylonitrile butadiene styrene (ABS), polysulphone, or the like; Polynorbonene; other deformable polymers; or any other shape memory polymer.

As shown in FIG. 1B, the shape memory material 130 may be located in the fluid impermeable barrier 102, such as being incorporated into the fluid impermeable barrier 102. In an embodiment, the shape memory material 130 may comprise a shape memory polymer incorporated into the fluid impermeable barrier 102, such as in a mixture of a shape memory polymer and the material of the fluid impermeable barrier 102. The amount of shape memory polymer in the fluid impermeable barrier 102 may be present in an amount sufficient to maintain the fluid collection device 100 in a selected shape during use. In an example, the amount of shape memory polymer in the fluid impermeable barrier 102 may be at least 10 wt % of the total weight of the fluid impermeable barrier 102, such as 10 wt % to 90 wt %, 10 wt % to 50 wt %, 10 wt % to 30 wt %, 30 wt % to 60 wt %, 60 wt % to 90 wt %, or less than 90 wt % of the total weight of the fluid impermeable barrier 102. In an example, the material of the fluid impermeable barrier 102 may be solely shape memory polymer. In an embodiment, the shape memory material 130 may comprise a shape memory metal (e.g., aluminum, copper, etc.) incorporated into the fluid impermeable barrier 102, such as in a mixture of a shape memory metal and the material of the fluid impermeable barrier 102. In an embodiment, the material of the fluid impermeable barrier 102 may be solely shape memory metal.

Figure 1C:
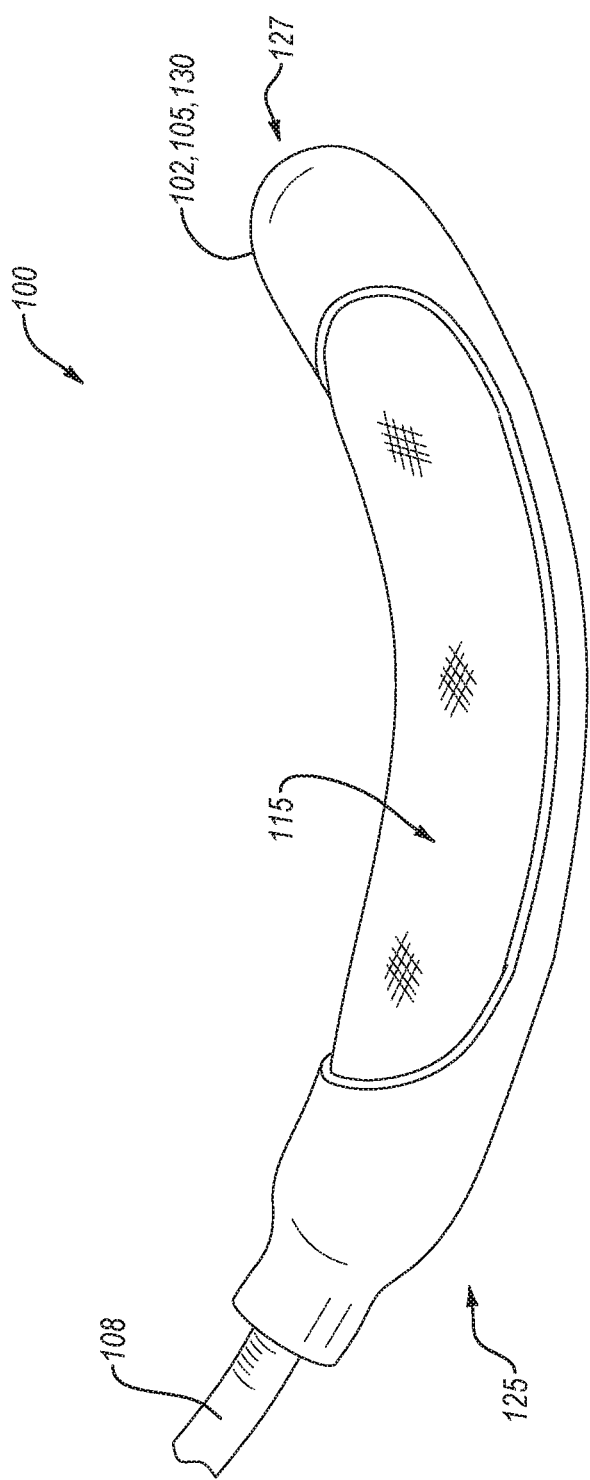
FIG. 1C is an isometric view of the fluid collection device of FIG. 1A, according to an embodiment.

Although FIGS. 1A-1C illustrate that the shape memory material 130 is incorporated in the fluid impermeable barrier 102, it is noted that the shape memory material 130 may be incorporated into other components of the fluid collection device 100. In an embodiment, the shape memory material 130 is incorporated in the conduit 108 and/or the porous material 115. The shape memory material 130 may be incorporated into the conduit 108 and/or the porous material 115 in any of the same manners as discussed above with regards to incorporating the shape memory material 130 into the fluid impermeable barrier 102. For example, the amount of the shape memory material 130 may be at least 10 wt % of the total weight of the conduit 108 and/or the porous material 115 or the material of the conduit 108 and/or the porous material 115 may solely include the shape memory material 130. Incorporating the shape memory material 130 into the conduit 108 and/or the porous material 115 may cause the conduit 108 to conform to the general shape of the fluid collection device 100 after the fluid collection device 100 is shaped. For example, as will be discussed in more detail with regards to FIGS. 9A and 9B, incorporating the shape memory material 130 into the conduit 108 and/or the porous material 115 cause the conduit 108 to conform to the shaping of the fluid collection device 100 without the use of braces.

In some examples, the shape memory material 130 may only be disposed in one or more discrete portions of the fluid impermeable barrier 102. For example, the fluid impermeable barrier 102 may be at least partially constructed of shape memory material 130 longitudinally extending along the bottom surface (e.g., substantially opposite the opening) of the fluid collection device 100.

FIG. 1C is an isometric view of the fluid collection device 100 of FIG. 1A, according to an embodiment. FIG. 1C shows the fluid collection device 100 in a second shape which differs from the first shape shown in FIG. 1A. As shown, the fluid collection device 100 may be shaped to contour to the anatomy of a wearer using the fluid collection device 100 to improve comfort over conventional devices and to remain in position during use. The fluid collection device 100 may be manipulated to contour to the anatomy in the groin region of a wearer. For example, the second end region 127 may be shaped upwardly such that the fluid collection device 100 maintains a generally arcuate shape with the first end region 125 and the second end region being disposed above a medial portion therebetween. In such examples, the second end region may be positioned in the gluteal cleft of the wearer, the second end region may be positioned against the upper vaginal or pubic area of the wearer, and the portion therebetween may be shaped to contour the anatomy of the wearer. The shape in the device may be more or less arcuate depending on the size and shape of the wearer. Accordingly, the devices disclosed herein may be utilized with a variety of differently sized wearers.

Additionally, the fluid collection device 100 may be returned to an original shape (e.g., a substantially straight cylinder) or manipulated into a third shape after being manipulated and used in the second shape. Such manipulation may be performed by applying a stimuli, such as any of those disclosed herein.

In an example, one or more components (e.g., fluid impermeable barrier 102, conduit 108, the porous material 115, etc.) of the fluid collection device 100 may include an odor blocking or absorbing material such as a cyclodextrine-containing material or a thermoplastic elastomer (TPE) polymer.

Other embodiments of fluid impermeable barriers, fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. Pat. No. 10,225,376 filed on Jun. 1, 2017, the disclosure of each of which is incorporated herein, in its entirety, by this reference.

In some embodiments, the shape memory material in the fluid collection device 100 may be located in one or more different or additional locations than those depicted in FIGS. 1A to 1C. For example, the shape memory material 130 used fluid collection devices disclosed may be distinct from the other components of the fluid impermeable barriers (e.g., the fluid impermeable barrier, the porous material, and/or the conduit). The shape memory materials that are distinct from the other components of the fluid impermeable barriers may be used instead of or in conjunction with the shape memory materials that are included in the one or more components of the fluid impermeable barrier.

Figure 2A:
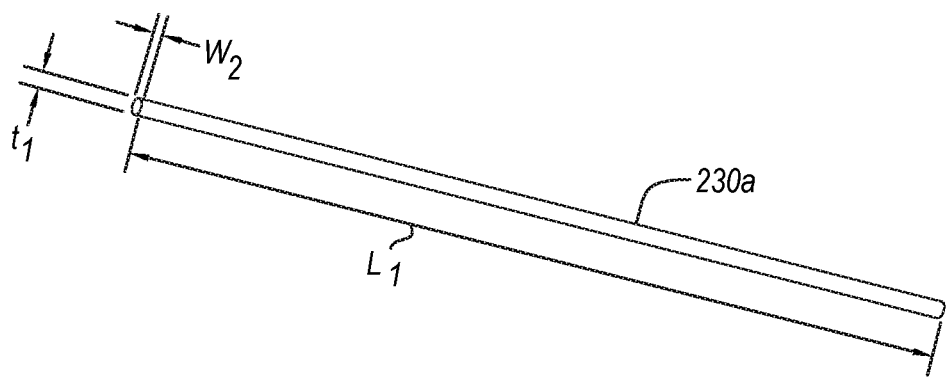
FIGS. 2A to 2C are isometric views of shape memory materials that are distinct from the other components of the fluid impermeable barrier, according to different embodiments.
Figure 2B:
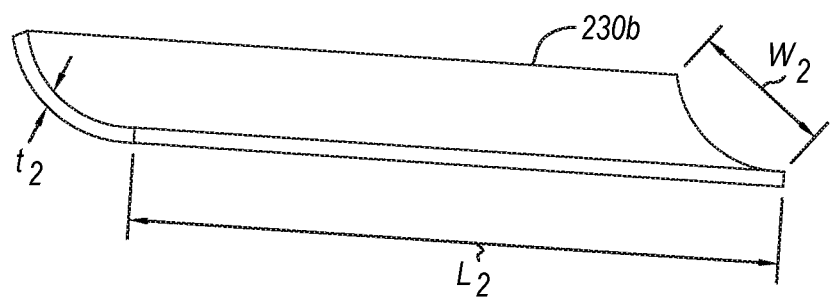
Figure 2C:
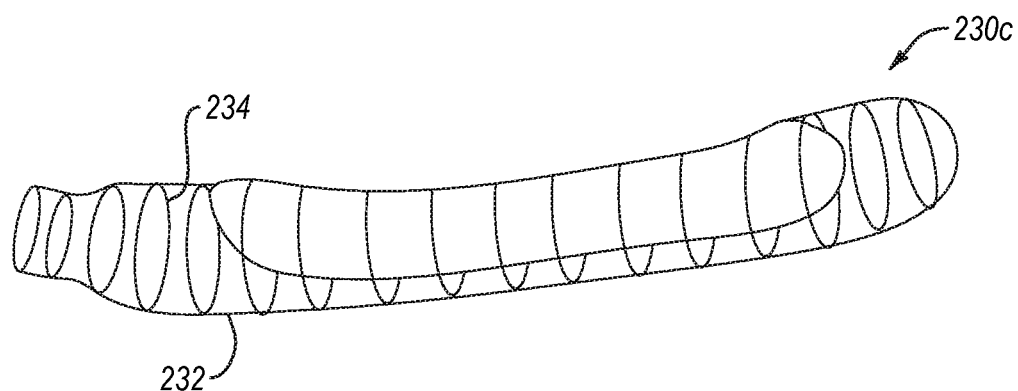

FIGS. 2A to 2C are isometric views of shape memory materials that are distinct from the other components of the fluid impermeable barrier, according to different embodiments. Except as otherwise disclosed herein, the shape memory materials shown in FIGS. 2A-2C are the same or substantially similar to any of the shape memory materials disclosed herein. For example, the shape memory materials shown in FIGS. 2A-2C may include any of materials disclosed herein or may be configured to be shaped using any the stimuli disclosed herein. Further, except as otherwise disclosed herein, the shape memory materials shown in FIGS. 2A-2C may be used in any of the fluid collection devices disclosed herein.

Referring to FIG. 2A, the shape memory material 230a includes at least one wire (e.g., at least one rod). The wire includes a length $L_1$ measured along a longitudinal axis of the wire, a width $W_1$ measured perpendicularly to the length $L_1$, and a thickness $t_1$ measured perpendicularly to the length $L_1$ and the width $W_1$. The length $L_1$ of the wire is significantly greater than the width $W_1$ and the thickness $t_1$. In an embodiment, the wire is sized and configured such that the length $L_1$ is generally aligned with the longitudinal axis of the fluid impermeable barrier. In such an embodiment, the wire can change the shape of the fluid collection device along the longitudinal axis thereof and/or change the shape of the fluid impermeable barrier globally. In an embodiment, the wire is sized and configured to such that the length $L_1$ is not aligned with the longitudinal axis of the fluid impermeable barrier (e.g., the length $L_1$ is generally perpendicular to the longitudinal axis of the fluid collection device). In such an embodiment, the wire may at least one of extend between and interconnect a plurality of wires that have lengths that are generally aligned with the longitudinal axis of the fluid impermeable barrier, allow the wire to change the shape of the fluid collection device along an axis that is different than the longitudinal axis of the fluid collection device, or facilitate local changes in the shape of the fluid impermeable barrier.

The length of the wire may be at least 10% of the longitudinal length of the fluid collection device, such as 10% to 100%, 30% to 100%, 10% to 40%, 30% to 60%, 60% to 90%, 40% to 80%, 50% to 100%, less than 100%, or less than 70% of the length of the fluid collection device. In an example, the wire may exhibit a generally circular cross-sectional shape. In such an example, the width $W_1$ and the thickness $t_1$ are the same. In an example, the wire may exhibit a slightly oblong cross-sectional shape. In such an example, the width $W_1$ may be slightly greater (e.g., at most about 50% greater, at most about 25% greater, or at most 10% greater) than the thickness $t_1$. The width $W_1$ and the thickness $t_1$ may be at least 0.5 mm, such as about 0.5 mm to about 1.5 mm, about 1 mm to about 2 mm, about 1.5 mm to about 2.5 mm, about 2 mm to about 3 mm, about 2.5 mm to about 3.5 mm, about 3 mm to about 4 mm, about 3.5 mm to about 4.5 mm, about 4 mm to about 5 mm, about 4.5 mm to about 6 mm, about 5 mm to about 7 mm, about 6 mm to about 8 mm, about 7 mm to about 9 mm, about 8 mm to about 10 mm, about 9 mm to about 1.2 cm, about 1 cm to about 1.5 cm, about 1.25 cm to about 1.75 cm, about 1.5 cm to about 2 cm, about 1.75 cm to about 2.5 cm, or about 2 cm to about 3 cm.

Referring to FIG. 2B, the shape memory material 230*b* includes a plate (e.g., strip). The plate exhibits a length $L_2$, a width $W_2$, and a thickness $t_2$. The length $L_2$ of the plate may be the same as or substantially similar to any of the lengths disclosed herein. Similar to the shape memory material 230*a* of FIG. 2A, the plate may be configured such that the length $L_2$ thereof is aligned or not aligned with the longitudinal axis of the fluid collection device. The width $W_2$ of the plate is greater (e.g., at least 50% greater) than the thickness $t_2$. The width $W_2$ may be at least 3% of the lateral width of the fluid collection device, such as 3% to 100%, 3% to 50%, 3% to 20%, 20% to 40%, 40% to 60%, 60% to 80%, 80% to 100%, less than 100%, or less than 50% of the width of the fluid collection device. The thickness $t_2$ may be the same as or substantially similar to any of the thicknesses disclosed herein.

In an embodiment, the plate may initially (i.e., before shaping the plate) exhibit one or more bends therein (e.g., the plate is an at least partial tube). For example, as illustrated, the plate may exhibit a bend in the direction that is parallel to the width $W_2$. The bend in the plate may be configured to correspond to the shape of the fluid collection device. For example, at least some of the fluid collection devices disclosed herein exhibit a generally cylindrical shape and the bend in the plate may correspond to the curvature of the generally cylindrical shape of the fluid collection device. However, the bend in the plate may make shaping the plate more difficult. In an embodiment, the plate may be substantially planar.

In an embodiment, the plate may have one or more openings or perforations therein. For example, depending on the location of the plate in the fluid collection device, the one or more openings or perforations may allow fluid to flow to through the plate. The one or more openings or perforations may also decrease the weight of the plate. The one or more openings or perforations may also weaken the plate thereby facilitating shaping of the plate to form regions of the plate that are preferentially shaped relative to other regions of the plate.

The plate may provide more support to the fluid collection device thereby allowing the fluid collection device to better maintain the desired shape thereof compared to the wire. However, the plate may be more difficult to shape than the wire and may be shaped in fewer directions than the wire due to the increased cross-sectional area of the plate relative to the wire.

Referring to FIG. 2C, the shape memory material 230*c* includes a plurality of interconnected wires (e.g., the shape memory material 230*c* is a wire mesh). Each of the plurality of interconnected wires may be the same or substantially similar to any of the wires disclosed herein. The plurality of wires are interconnected with the plurality of wires are attached to, contact, or are positioned proximate to each other.

The shape memory material 230*c* may include at least one longitudinal wire 232 extending in a longitudinal direction of the shape memory material 230*c*. Generally, the longitudinal wire 232 is generally aligned with the longitudinal axis of the fluid collection device though, it is noted, that the longitudinal wire 232 may not be generally aligned with the longitudinal axis of the fluid collection device. The shape memory material 230*c* also includes at least one transverse wire 234 extending in a direction that is different than the longitudinal wire 232. For example, the transverse wire 234 may extend generally perpendicularly to the longitudinal wire 232, such as in a circumferential direction.

The longitudinal wire 232 and the transverse wire 234 may generally exhibit the shape of a portion of the fluid collection device. For example, in the illustrated embodiment, the longitudinal wire 232 and the transverse wire 234 exhibit the generally shape of a portion of the fluid collection device 100 shown in FIG. 1A, including an unoccupied gap for the opening 106. It is noted that the longitudinal wire 232 and the transverse wire 234 may also generally exhibit the shape of the fluid collection device illustrated in FIG. 12A.

It is noted that any of the fluid collection devices disclosed herein may include a plurality of shape memory materials that include the shape memory materials disclosed herein. For example, the shape memory material for any of the fluid collection devices disclosed herein may include a plurality of wires, a plurality of plates, a plurality of interconnected wires, or combinations thereof. It is also noted that the shape memory materials illustrated in FIGS. 2A-2C are merely examples of shape memory materials that may be distinct from the other components of the fluid collection device. For example, the shape memory materials that are distinct from the other components of the fluid collection device may include a plurality of interconnected plates, one or more annular rings, a tube, a coating, a mesh-like structure, a sheet, any other suitable structure, or combinations thereof.

Figure 3:
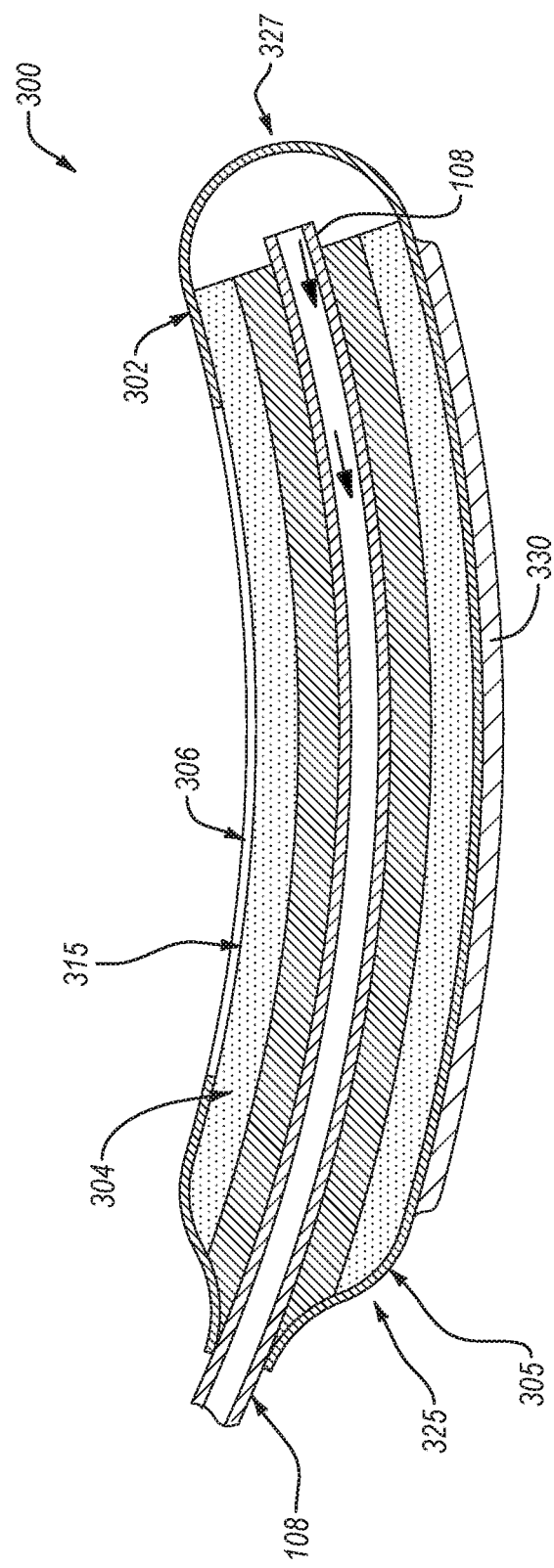
FIG. 3 is a cross-sectional view of a fluid collection device, according to an embodiment.

FIG. 3 is a cross-sectional view of a fluid collection device 300, according to an embodiment. Except as otherwise disclosed herein, the fluid collection device 300 is the same or substantially similar to the fluid collection device 100, in one or more aspects. For example, the fluid collection device 300 includes the fluid impermeable barrier 302, the porous material 315, and the conduit 108 as disclosed herein. The shape memory material 330 is disposed on the outer surface 305 of the fluid impermeable barrier 302. The shape memory material 330 may be distinct from the fluid impermeable barrier 302, the porous material 315, and the conduit 108. For example, the shape memory material 330 may include longitudinally extending elements. The shape memory material 330 may be adhered to one or more portions of the outer surface 305 the fluid impermeable barrier 302. For example, the shape memory material 330 may be bonded to the lower portion (e.g., the back of the device opposite the opening 306) of the fluid impermeable barrier 302. By positioning the shape memory material 330 in the lower portion of the fluid collection device 300, the relatively more rigid shape memory material 330 may not contact the wearer, thereby reducing or eliminating discomfort when worn. The shape memory material 330 may extend from the first end region 325 to the second end region 327. Accordingly, the shape memory material 330 on the fluid collection device 300 may be formed to, and maintain, a selected shape.

The shape memory material 330 may be the same or substantially similar to any of the shape memory materials disclosed herein. For example, the dimensions of the shape memory material 330 disposed on the fluid impermeable barrier 302 are sufficient to maintain the selected shape of the fluid collection device 300 when in use. The thickness, height, and length of the shape memory material 330 may be as disclosed herein with respect to the fluid collection device 300. The shape memory material 330 may also include any of the materials disclosed herein. The shape memory material may be coated in a relatively softer material, such as silicone or another polymer. The shape memory material 330 may also include a single structure (e.g., a single wire or plate) or a plurality of structures (e.g., a plurality of wires and/or plates) disposed the fluid impermeable barrier 302.

While being shown as being only in the lower half (e.g., back portion) of the fluid impermeable barrier 302, the shape memory material 330 may be disposed in the lateral portions or in the upper half (e.g., front, wearer-facing portion) of the fluid impermeable barrier 302 or may be an at least partial tube concentrically disposed on (e.g., covering at least a portion of) the fluid impermeable barrier 302.

Figure 4A:
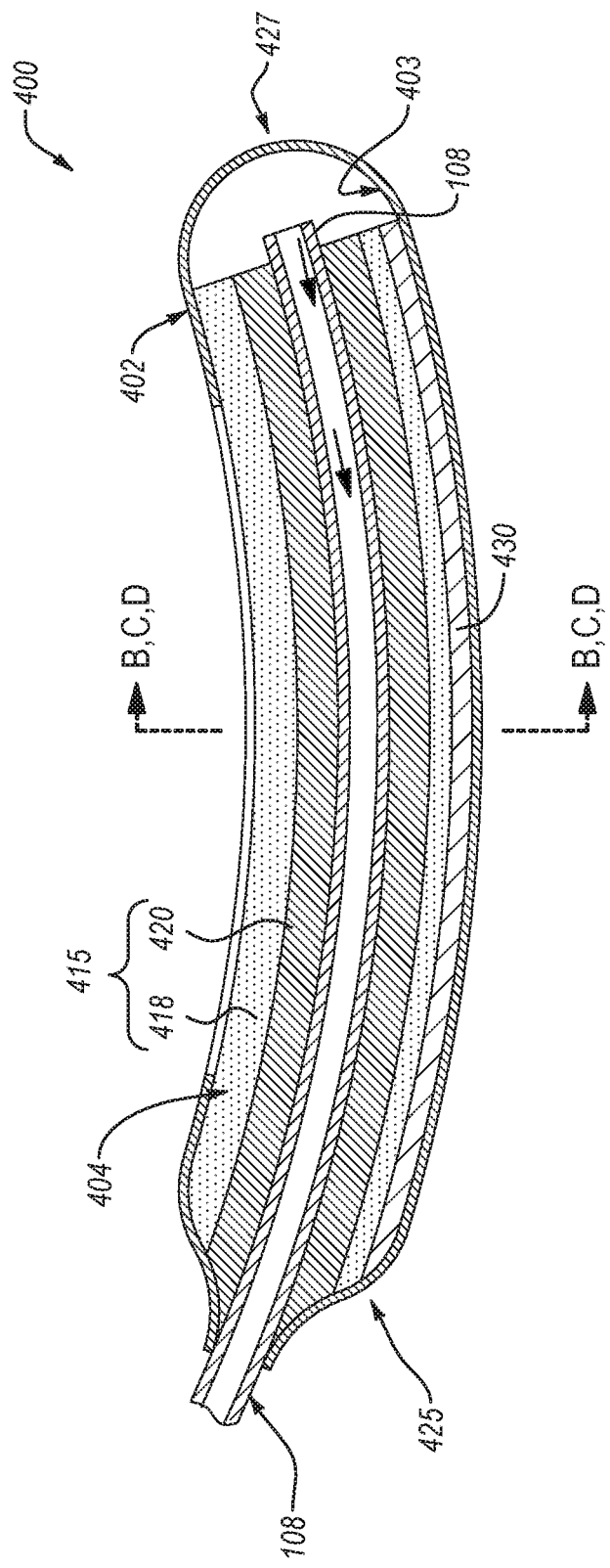
FIG. 4A is a cross-sectional view of a fluid collection device, according to an embodiment.

In some examples, the shape memory material may be disposed in the chamber. FIG. 4A is a cross-sectional view of a fluid collection device 400, according to an embodiment. Except as otherwise disclosed herein, the fluid collection device 400 is the same or substantially similar to one or more of fluid collection devices 100 or 300, in one or more aspects. For example, the fluid collection device 400 includes the fluid impermeable barrier 402, the porous material 415 (e.g., the fluid permeable membrane 418 and the fluid permeable support 420), the conduit 108 as disclosed herein. The shape memory material 430 is disposed on the inner surface 403 of the fluid impermeable barrier 402. The shape memory material 430 may be disposed between the fluid impermeable barrier 402 and the porous material 415, such as the fluid permeable membrane 418. The shape memory material 430 may distinct from the fluid impermeable barrier 402, the porous material 415, and the conduit 108. The shape memory material 430 may be adhered to one or more portions of the outer surface 405 of the fluid impermeable barrier 402. For example, the shape memory material 430 may be bonded to the lower (e.g., back) portion of the inner surface 403 of the fluid impermeable barrier 402. The shape memory material 430 may extend from the first end region 425 to the second end region 427. Accordingly, the shape memory material 430 on the fluid collection device 400 may be formed to, and maintain, a selected shape. By disposing the shape memory material 430 inside of the fluid impermeable barrier 402, the shape memory material 430 may not provide a perceptible feel on the skin of the wearer.

The shape memory material 430 may be the same or substantially similar to any of the shape memory materials disclosed herein. For example, the dimensions of the shape memory material 430 disposed in the chamber 404 are sufficient to maintain the selected shape of the fluid collection device 400 when in use. The shape memory material 430 may also include any of the materials disclosed herein. The shape memory material 430 may also include a single structure or a plurality of structures disposed on the inner surface 403.

While being shown as being only in the lower half (e.g., back portion) of the inner surface 403 of the fluid impermeable barrier 402, the shape memory material 430 may be disposed in the lateral portions or in the upper half (e.g., front, wearer-facing portion) of the inner surface 403 or may be an at least partial tube concentrically disposed on the inner surface 403.

Figure 4B:
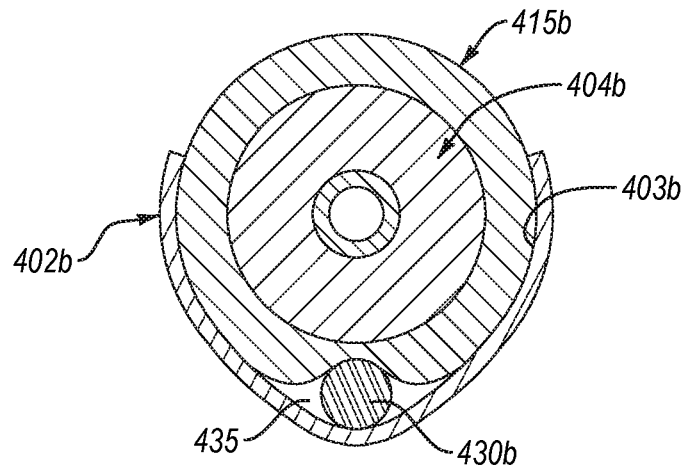
FIGS. 4B to 4D are cross-sectional view of the fluid collection device taken along the plane B,C,D-B,C,D of FIG. 4A, according to different embodiments.
Figure 4C:
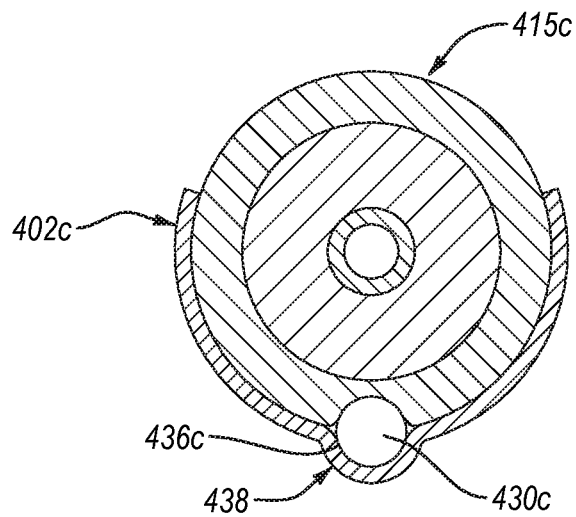
Figure 4D:
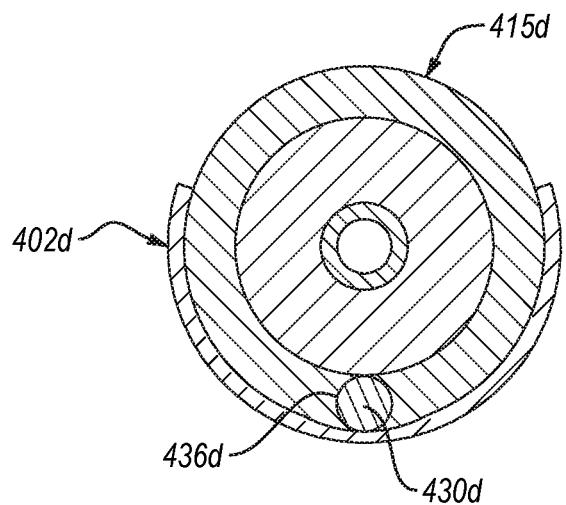

At least one of the fluid impermeable barrier 402 or the porous material 415 may be configured to accommodate the shape memory material 430. FIGS. 4B to 4D are cross-sectional view of the fluid collection device 400 taken along the plane B,C,D-B,C,D of FIG. 4A, according to different embodiments. FIGS. 4B-4D illustrate how at least one of the fluid impermeable barrier 402 or the porous material 415 accommodate the shape memory material 430. Referring to FIG. 4B, the chamber 404b exhibits a shape (e.g., generally cylindrical shape) and the porous material 415b exhibits a shape that corresponds to the shape of the chamber 404b. The shape memory material 430b is disposed in the chamber 404b between the fluid impermeable barrier 402b and the porous material 415b such that the shape memory material 430b is adjacent to (e.g., attached to) the inner surface 403b of the fluid impermeable barrier 402b. To accommodate the shape memory material 430b, a portion of the porous material 415b adjacent to the shape memory material 430b is compressed. Compressing the porous material 415b may at least one of decrease the volume of the porous material 415b or increase the density of the porous material 415b, either of which may decrease the amount of fluid that may be held by the porous material 415b. Compressing the porous material 415b may also cause voids 435 to form adjacent to the shape memory material 430b which provides locations for the fluid to detrimentally pool.

Referring to FIG. 4C, the fluid impermeable barrier 402c defines at least one recess 436c. The recess 436c may be formed by decreasing the thickness of the fluid impermeable barrier 402c or, as illustrated, the fluid impermeable barrier 402c may include at least one protrusion 438 that defines the recess 436c. The recess 436c is configured to have the shape memory material 430c at least partially disposed therein. As such, the recess 436c may exhibit a shape that generally corresponds to the shape of the shape memory material 430c. Positioning the shape memory material 430c in the recess 436c prevents the shape memory material 430c from compressing the porous material 415c when the recess 436c receives all of the shape memory material 430c or compresses the porous material 415c less than the shape memory material 430b shown in FIG. 4B when the recess 436c only receives a portion of the shape memory material 430c.

Referring to FIG. 4D, the porous material 415d (e.g., at least one of the fluid permeable membrane or the fluid permeable support) defines at least one recess 436d instead of or in conjunction with the fluid impermeable barrier 402d. The recess 436d is configured to have the shape memory material 430d at least partially disposed therein. As such, the recess 436d may exhibit a shape that generally corresponds to the shape of the shape memory material 430d. Positioning the shape memory material 430d in the recess 436d prevents the shape memory material 430d from compressing the porous material 415d when the recess 436d exhibits a size that is sufficient to receive all of the shape memory material 430d or compresses the porous material 415d less than the shape memory material 430b shown in FIG. 4B when the recess 436d exhibits a size that is sufficient to only receives a portion of the shape memory material 430d.

Figure 5:
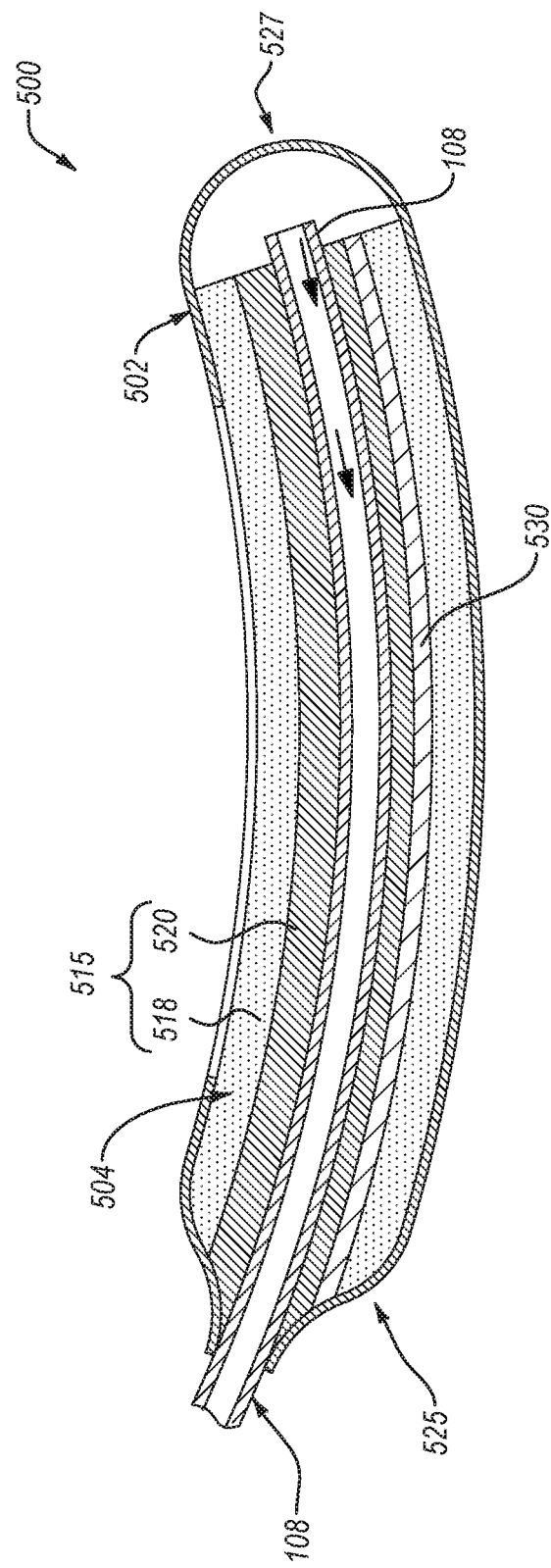
FIG. 5 is a cross-sectional view of a fluid collection device, according to an embodiment.

In some examples, the shape memory material may be disposed within the porous material. FIG. 5 is a cross-sectional view of a fluid collection device, according to an embodiment. Except as otherwise disclosed herein, the fluid collection device 500 is the same or substantially similar to one or more of fluid collection devices 100, 300, or 400, in one or more aspects. For example, the fluid collection device 500 includes the fluid impermeable barrier 502, the porous material 515, the conduit 108 as disclosed herein. The shape memory material 530 is disposed within the chamber 504 and spaced from the fluid impermeable barrier 502 along at least a portion of the length of the shape memory material 530 (e.g., a portion of the shape memory material 530 may contact the fluid impermeable barrier 502, such as a terminal end of the shape memory material 530). The shape memory material 530 is disposed within the porous material 515. For example, the shape memory material 530 may between the fluid permeable membrane 518 and the fluid permeable support 520, within the fluid permeable membrane 518, or within the fluid permeable support 520. The shape memory material 530 may include one or more longitudinally extending elements of shape memory material 530, as disclosed herein. The shape memory material 530 may be bonded to fluid permeable support 520, the fluid permeable membrane 518, or both. The shape memory material 530 may extend from the first end region 525 to the second end region 527. Accordingly, the shape memory material 530 on the fluid collection device 500 may be formed to, and maintain, a selected shape. By locating the shape memory material 530 within the chamber 504 and spaced from the fluid impermeable barrier 502, the shape memory material 530 may not provide a perceptible feel on the skin of the wearer when in use. In an embodiment, the porous material 515 may define a recess that is configured to at least partially receive the shape memory material 530.

The shape memory material 530 may be the same or substantially similar to any of the shape memory materials disclosed herein. For example, the dimensions of the shape memory material 530 disposed in the porous material 515 are sufficient to maintain the selected shape of the fluid collection device 500 when in use. The shape memory material 530 may also include any of the materials disclosed herein. The shape memory material 530 may also include a single structure or a plurality of structures disposed in the porous material 515.

While being shown as being only in the lower half (e.g., back portion) of the porous material, the shape memory material 530 may be disposed in the lateral portions or in the upper half (e.g., front, wearer-facing portion) of the porous material 515 or may be an at least partial tube concentrically disposed within the porous material 515.

Figure 6:
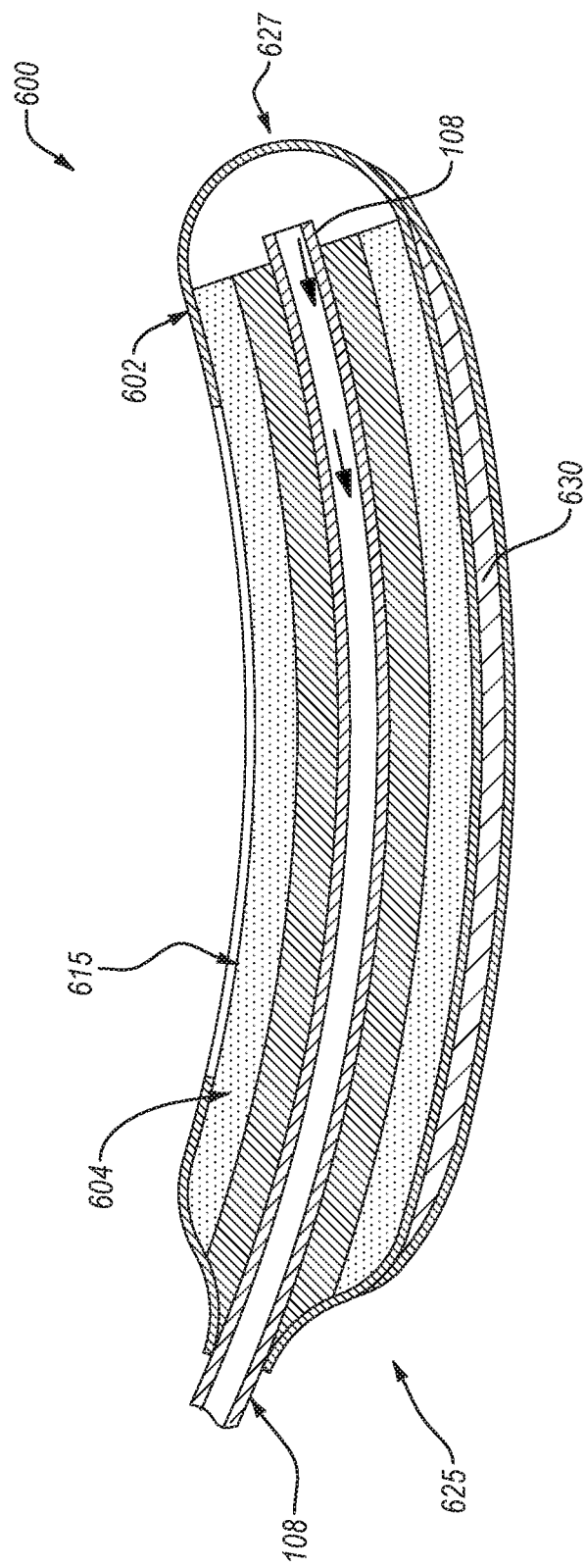
FIG. 6 is a cross-sectional view of a fluid collection device, according to an embodiment.

In some examples, the shape memory material may be incorporated into the fluid impermeable barrier, such as located external to the chamber and within the fluid impermeable barrier. FIG. 6 is a cross-sectional view of a fluid collection device 600, according to an embodiment. Except as otherwise disclosed herein, the fluid collection device 600 is the same or substantially similar to one or more of fluid collection devices 100 or 300-500, in one or more aspects.

For example, the fluid collection device 600 includes the fluid impermeable barrier 602, the porous material 615, and the conduit 108 as disclosed herein. The shape memory material 630 is disposed outside of the chamber 604 and incorporated within the fluid impermeable barrier 602. For example, the shape memory material 630 may be separate from, but at least partially embedded within, the fluid impermeable barrier 602. The shape memory material 630 may be overmolded into the fluid impermeable barrier 602. Accordingly, the shape memory material 630 may be isolated within the fluid impermeable barrier 602. In some examples, the shape memory material 630 may be bonded to fluid impermeable barrier 602 and a second portion of the fluid impermeable barrier 602 may be disposed on and over the shape memory material 630. The shape memory material 630 may extend from the first end region 625 to the second end region 627. Accordingly, the shape memory material 630 on the fluid collection device 600 may be formed to, and maintain, a selected shape. By locating the shape memory material 630 within the fluid impermeable barrier 602, the shape memory material 630 may not provide a perceptible feel on the skin of the wearer when in use and the shape memory material 630 may be isolated from the fluids in the chamber 604.

The shape memory material 630 may be the same or substantially similar to any of the shape memory materials disclosed herein. For example, the dimensions of the shape memory material 630 disposed in the fluid impermeable barrier 602 are sufficient to maintain the selected shape of the fluid collection device 600 when in use. The shape memory material 630 may also include any of the materials disclosed herein. The shape memory material 630 may also include a single structure or a plurality of structures disposed in the fluid impermeable barrier 602.

While being shown as being only in the lower half (e.g., back portion) of the fluid impermeable barrier 602, the shape memory material 630 may be disposed in the lateral portions or in the upper half (e.g., front, wearer-facing portion) of the fluid impermeable barrier 602 or may be an at least partial tube concentrically disposed within the fluid impermeable barrier 602.

Figures 7A, 7B:
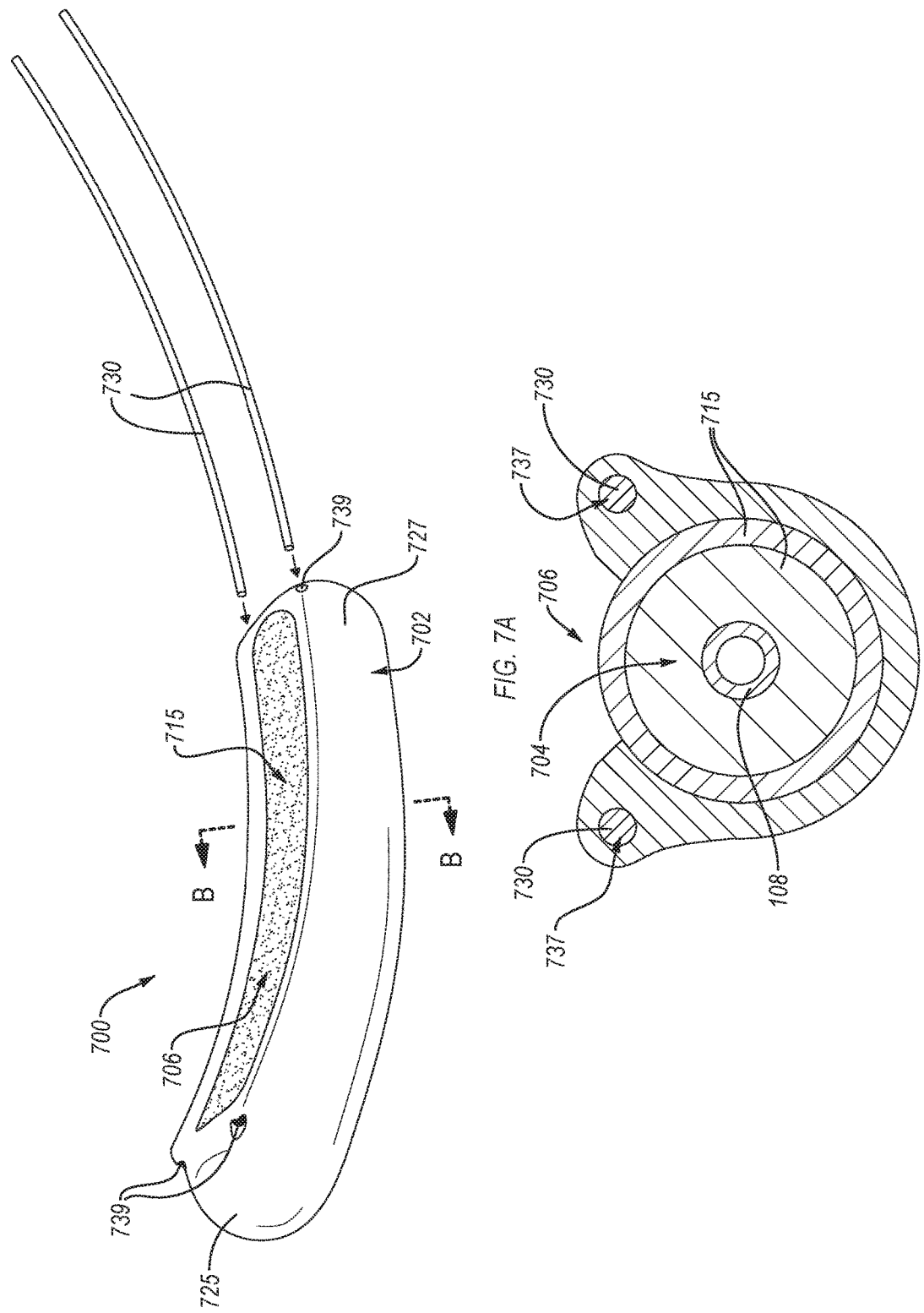
FIG. 7A is an isometric view of a fluid collection device illustrating at least one shape memory material being inserted into and/or removed from the fluid impermeable barrier, according to an embodiment.
FIG. 7B is a cross-sectional schematic view of the fluid collection device taken along the plane B-B of FIG. 7A with the shape memory material disposed in the fluid impermeable barrier, according to an embodiment.

In some examples, the fluid impermeable barrier may define a cavity and at least one aperture that allows a shape memory material to be inserted into and removed from the cavity. FIG. 7A is an isometric view of a fluid collection device 700 illustrating at least one shape memory material 730 being inserted into the fluid impermeable barrier 702, according to an embodiment. FIG. 7B is a cross-sectional schematic view of the fluid collection device 700 taken along the plane B-B of FIG. 7A with the shape memory material 730 disposed in the fluid impermeable barrier 702, according to an embodiment. Except as otherwise disclosed herein, the fluid collection device 700 is the same or substantially similar to one or more of fluid collection devices 100 or 300-600, in one or more aspects. For example, the fluid collection device 700 includes the fluid impermeable barrier 702, the porous material 715, and the conduit 108 as disclosed herein.

The shape memory material 730 is disposed outside of the chamber 704. The fluid impermeable barrier 702 defines at least one cavity 737 and the shape memory material 730 is disposed in the cavity 737. The cavity 737 may exhibit a size and shape that allows the cavity 737 to receive at least a portion (e.g., all or substantially all) of the shape memory material 730 therein. For example, the cavity 737 may exhibit a cross-sectional shape that is the same as or slightly larger than the shape memory material 730 such that friction maintains the shape memory material 730 in the cavity 737 during normal operations. The fluid impermeable barrier 702 also defines at least one aperture 739. The aperture 739 is configured to allow access to the cavity 737 such that the shape memory material 730 may be inserted into and/or removed from the cavity 737. Each cavity 737 may include a single aperture 739 or a plurality of apertures 739 (e.g., an aperture 739 on opposing ends of the cavity 737). Further, by locating at least a portion of the shape memory material 730 within the cavity 737 (e.g., within the fluid impermeable barrier 700), the shape memory material 730 may not provide a perceptible feel on the skin of the wearer when in use and the shape memory material 730 may be isolated from the fluids in the chamber 704.

The cavity 737 and the aperture 739 allow the shape memory material 730 to be inserted and/or removed from the cavity 737. In an example, the cavity 737 and the aperture 739 allow the shape memory material 730 to be replaced when damaged or misshaped. In an example, the cavity 737 and the aperture 739 may allow the shape memory material 730 to be shaped prior to inserting the shape memory material 730 into the cavity 737 which may be easier than shaping the shape memory material 730 while the shape memory material 730 is in the cavity 737. In an example, the cavity 737 and the aperture 739 may allow the shape memory material 730 to be selected for the particular wearer. In such an example, at least one of the shape memory material 730 may be selected to exhibit an initial shape that is substantially similar to the anatomy of the wearer thereby requiring little to no shaping of the shape memory material 730. In an example, the cavity 737 and the aperture 739 allows the shape memory material 730 to be reused (e.g., after washing the shape memory material 730). In such an example, the wearer may remove the shape memory material 730 from a fluid collection device that the wearer previously used and insert the shape memory material 730 into a new fluid collection device that the wearer will use. Inserting the previously used shape memory material 730 into the new fluid collection device may preclude the need to shape the shape memory material 730.

In an embodiment, the cavity 737 and the aperture 739 are sized such that a portion of the shape memory material 730 is accessible (e.g., an wearer can grab the shape memory material 730) after the shape memory material 730 is in the cavity 737. In an example, the cavity 737 may be exhibit a length that is smaller than the length of the shape memory material 730 such that a portion of the shape memory material 730 protrudes from the cavity 737. In an example, the aperture 739 may include a flap or other device that is able to switch between an open and closed state. In such an example, the flap or other device may cover the shape memory material 730 when in the closed state such that shape memory material 730 may not provide a perceptible feel on the skin of the wearer. However, the flap or other device may provide access to the shape memory material 730 when in the open state.

The shape memory material 730 may be the same or substantially similar to any of the shape memory materials disclosed herein. For example, the dimensions of the shape memory material 730 disposed in the fluid impermeable barrier 702 are sufficient to maintain the selected shape of the fluid collection device 700 when in use (e.g., the shape memory material 730 may extend from the first end region 725 to the second end region 727). The shape memory material 730 may also include any of the materials disclosed herein.

In the illustrated embodiment, the cavity 737 and the shape memory material 730 are shown being positioned adjacent to the opening 706. In such an embodiment, the fluid collection device 700 may include a plurality of cavities 737 and the shape memory material 730 may include a corresponding plurality of shape memory materials 730. However, it is noted that the shape memory material 730 may be disposed in the lateral portions or in the lower half of the fluid impermeable barrier 702.

Figure 8:
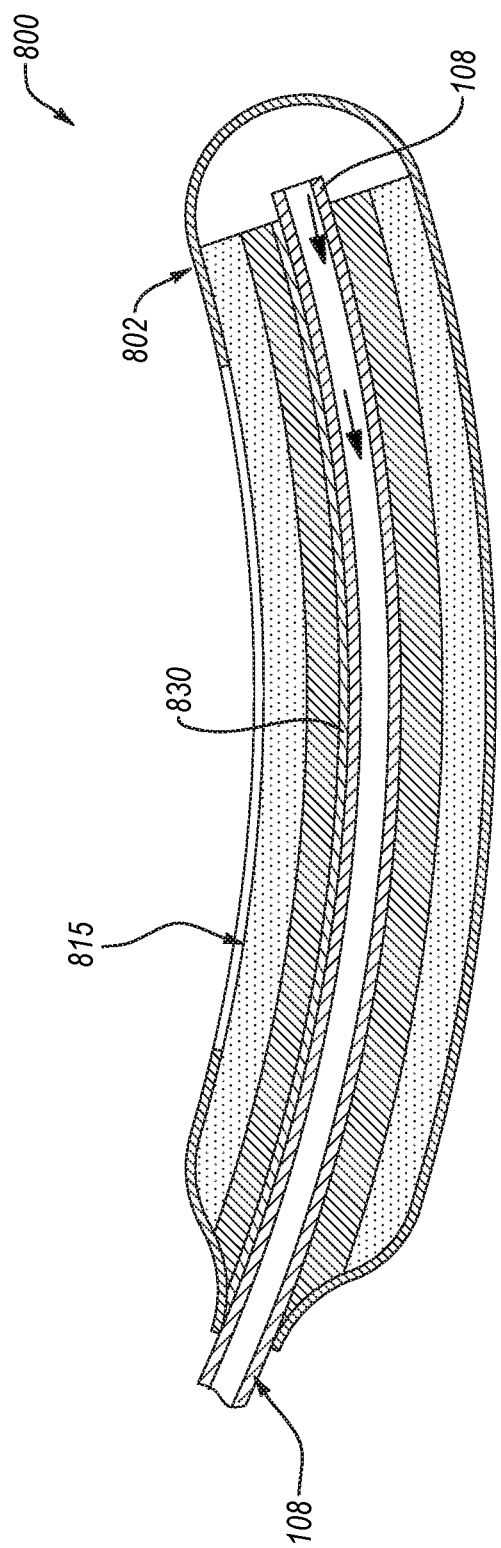
FIG. 8 is a cross-sectional view of a fluid collection device, according to an embodiment.

In some examples, the shape memory material may be positioned adjacent to the conduit. FIG. 8 is a cross-sectional view of a fluid collection device 800, according to an embodiment. Except as otherwise disclosed herein, the fluid collection device 800 is the same or substantially similar to one or more of fluid collection devices 100 or 300-700, in one or more aspects. For example, the fluid collection device 800 includes the fluid impermeable barrier 802, the porous material 815, and the conduit 108, as disclosed herein. The shape memory material 830 is disposed on (e.g., attached to or contacts) the conduit 108. The shape memory material 830 may be distinct from the conduit 108 and the porous material 815. The shape memory material 830 may include longitudinally extending elements. The shape memory material may be adhered (e.g., bonded) to one or more portions of an outer surface 838 of the conduit 108 or enclose the outer surface 838 of the conduit 108. Accordingly, the shape memory material 830 on the may be formed to, and maintain, a selected shape which, in turn, may cause the fluid collection device 800 to exhibit a shape that generally corresponds to the shape of the shape memory material 830. By disposing the shape memory material 830 on the conduit 108, the shape memory material 830 may not provide a perceptible feel on the skin of the wearer.

The shape memory material 830 may be the same or substantially similar to any of the shape memory materials disclosed herein. For example, the dimensions of the shape memory material 830 disposed on the conduit 108 are sufficient to maintain the selected shape of the fluid collection device 800 when in use. The shape memory material 830 may also include any of the materials disclosed herein. The shape memory material 830 may also include a single structure or a plurality of structures disposed on the conduit 108.

While being shown as being only in the lower half (e.g., back portion) of the conduit 108, the shape memory material 830 may be disposed in the lateral portions or in the upper half (e.g., front, wearer-facing portion) of the conduit 108 or may be an at least partial tube concentrically disposed on the conduit 108.

In an embodiment, the conduit may exhibit an initial shape when the conduit is in its relaxed state. The conduit is in its relaxed state when no external forces, such as forces caused by shaping the shape memory material, are applied to the conduit. The initial shape of the conduit may be a generally cylindrical shape (e.g., the conduit is straight) or a slightly curved generally cylindrical shape. Shaping the shape memory material may apply an external force to the conduit that causes the conduit to change the shape thereof. However, the conduit may resist changing the shape thereof when the external force are applied to the conduit which causes the conduit to apply a normal force that is opposite the external force. The normal force from the conduit may cause the conduit to compress a portion of the porous material and/or may cause the formation of detrimental voids in the chamber.

The fluid collection devices disclosed herein may include one or more structures that are configured to force the conduit to exhibit the desired shape change and minimize the normal force that is applied to the porous material. FIG. 9A is a cross-sectional view of a fluid collection device 900, according to an embodiment. FIG. 9B is a cross-sectional view of the fluid collection device 900 taken along plane B-B of FIG. 9A, according to an embodiment. Except as otherwise disclosed herein, the fluid collection device 900 is the same or substantially similar at any of the fluid collection devices disclosed herein. For example, the fluid collection device 900 includes a fluid impermeable barrier 902, a porous material 915, a conduit 108, and a shape memory material 930. In the illustrated embodiment, the fluid collection device 900 is illustrated as being substantially similar to the fluid collection device 400 shown in FIG. 4A. However, as previously discussed, the fluid collection device 400 may be substantially similar to any of the fluid collection devices disclosed herein.

The fluid collection device 900 includes at least one brace 940 that is configured to force the conduit 108 to exhibit a shape change that corresponds more closely to the shape change of the shape memory material 930 than if the fluid collection device 900 did not include the brace 940. The brace 940 also minimizes the normal force applied from the conduit 108 to the porous material 915. The brace 940 is connected to the shape memory material 930 or a component of the fluid collection device 900 that is connected to the shape memory material 930 (e.g., the fluid impermeable barrier 902 when the shape memory material 930 is attached to an exterior surface of or embedded within the fluid impermeable barrier 902). The brace 940 extends from the shape memory material 930 or the component of the fluid collection device 900 that is connected to the shape memory material 930 to the conduit 108. For example, the brace 940 may extend around the conduit 108, as shown in FIG. 9B. It is noted that the brace 940 may be attached to the conduit 108 using other suitable techniques, such as with an adhesive. To allow the brace 940 to extend to the conduit 108, one or more components of the fluid collection device 900 (e.g., the porous material 915) may include one or more slits formed therein through which the braces 940 extend. The brace 940 may be configured to transfer a shape change in the shape memory material 930 to the conduit 108 such that the conduit 108 exhibits a shape change that substantially corresponds to the shape change of the shape memory material 930.

The fluid collection device 900 may include any suitable number of braces 940, such as 1, 2, 3, 4, 5, 6, 7, 8, 9, 10, or greater than 10 braces 940. Generally increasing the number of braces 940 causes the conduit 108 to more accurately correspond to the shape of the shape memory material 930 and decreases the normal force that is applied to the porous material 915.

It is noted that the braces 940 may not always cause the conduit 108 to exhibit the same shape change as the shape memory material 930. For example, when the braces 940 are looped around and are not attached to the conduit 108 (as shown), the braces 940 may only cause the conduit 108 to exhibit the shape change of the shape memory material 930 when the braces 940 pull (e.g., the braces 940 are in tension) the conduit 108 towards the shape memory material 930 but not when the braces 940 push (e.g., the braces 940 are in compression) the conduit 108 away from the shape memory material 930.

In an embodiment, the braces 940 are formed from any of the shape memory materials disclosed herein. In an embodiment, the braces 940 may be formed from a non-shape memory material, such as fabric.

The fluid collection devices shown in FIGS. 1A-9B are examples of female fluid collection devices that are configured to collect fluid(s) from females (e.g., collect urine from a female urethra). However, the fluid collection devices, systems, and methods disclosed herein may include male fluid collection devices shaped, sized, and otherwise configured to collect fluid(s) from males (e.g., collect urine from a male urethra). FIGS. 10 to 15 are isometric and cross-sectional views of male fluid collection devices according to different embodiments.

Figure 10A:
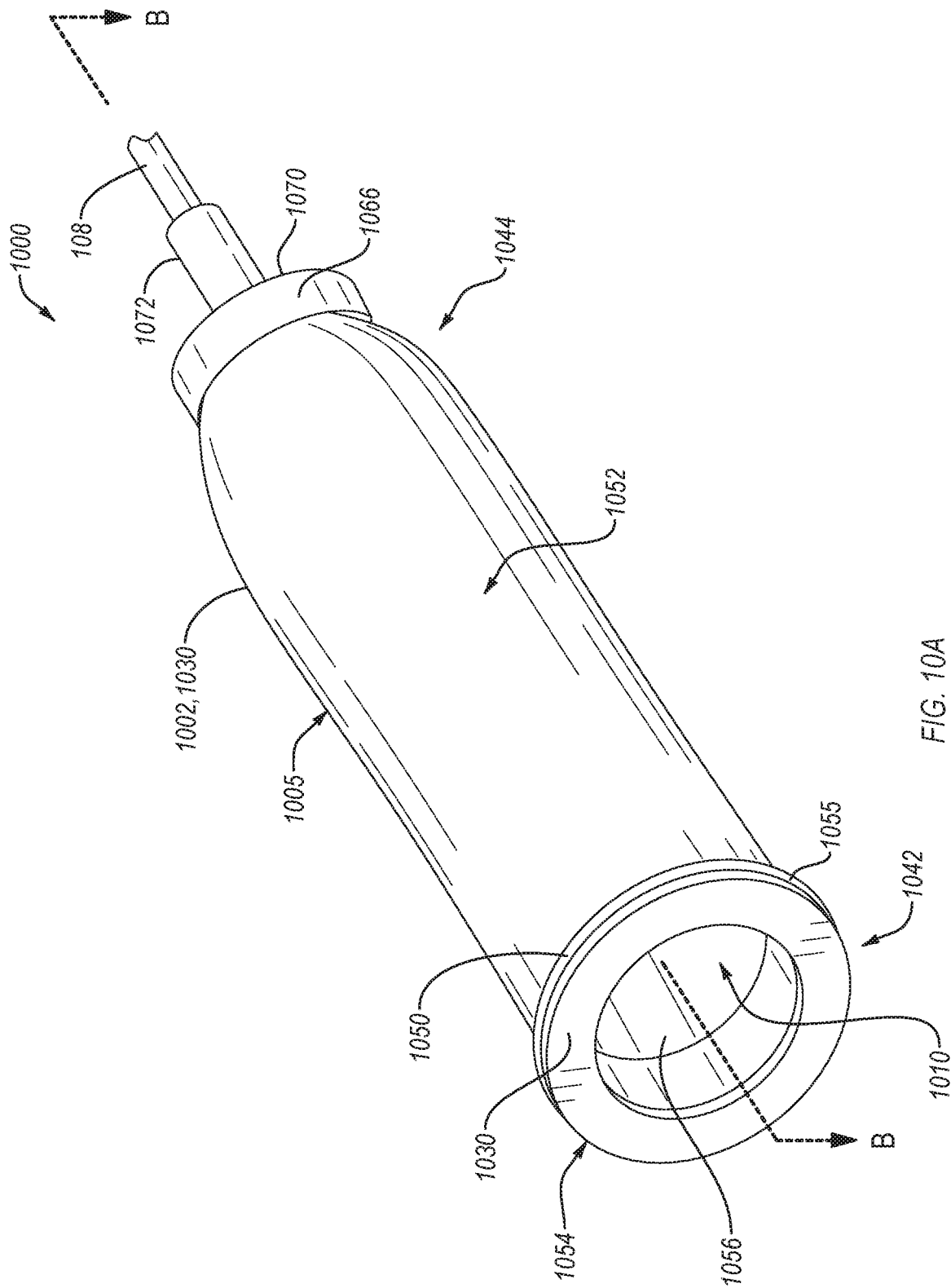
FIG. 10A is an isometric view of a fluid collection device according to an embodiment.
Figure 10B:
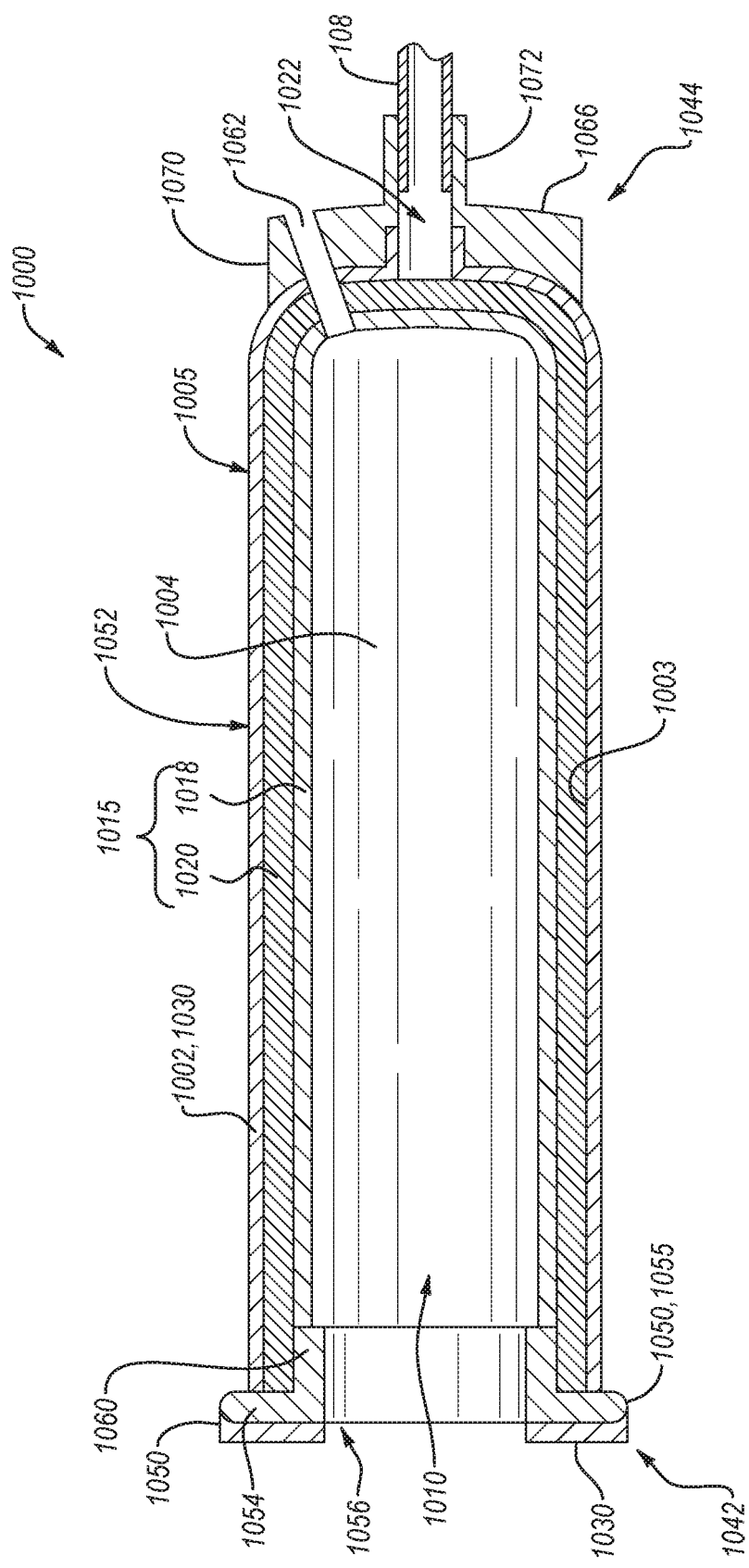
FIG. 10B is a cross-sectional view of the fluid collection device of FIG. 10A taken along the plane B-B of FIG. 10A, according to an embodiment.

FIG. 10A is an isometric view of a fluid collection device 1000 according to an embodiment. FIG. 10B is a cross-sectional view of the fluid collection device 1000 of FIG. 10A taken along the plane B-B of FIG. 10A, according to an embodiment. Referring to FIG. 10A and FIG. 10B, the fluid collection device 1000 includes a receptacle 1050 and a sheath 1052. The receptacle 1050 is sized, shaped, and made of a material to be coupled to skin that surrounds the male urethra and have the male urethra positioned therethrough. For example, the receptacle 1050 may include an annular base 1054 that defines an opening 1056 in the receptacle 1050. The annular base 1054 is sized and shaped to be positioned around the male urethra (e.g., positioned around and/or over the penis) and the opening 1056 may be configured to have the male urethra positioned therethrough. The annular base 1054 may also be sized, shaped, made of a material, or otherwise configured to be coupled (e.g., adhesively attached, such as with a hydrogel adhesive) to the skin around the male urethra (e.g., around the penis). In an example, the annular base 1054 may exhibit the general shape or contours of the skin surface that the annular base 1054 is selected to be coupled with. The annular base 1054 may be flexible thereby allowing the annular base 1054 to conform to any shape of the skin surface. The annular base 1054 may include a laterally extending flange 1055. The receptacle 1050 also defines a hollowed region that is configured to receive (e.g., seal against) the sheath 1052. For example, the receptacle 1050 may include a longitudinally extending flange 1060 that extends upwardly from the annular base 1054. The longitudinally extending flange 1060 may be tall enough to prevent the sheath 1052 from being accidentally removed from the receptacle 1050 (e.g., at least 0.25 cm tall, 1 cm tall, at least 10 cm tall, or at least 5 cm tall). The receptacle 1050 is located at a proximal region 1042 (with respect to a wearer) of the fluid collection device 1000.

The sheath 1052 includes (e.g., may be formed from) a fluid impermeable barrier 1002 that is sized and shaped to fit into the hollowed region of the receptacle 1050. For example, the sheath 1052 may be generally tubular or cup-shaped, as shown. The generally tubular or cup-shaped fluid impermeable barrier 102 may at least partially define the outer surface 1005 of the sheath 1052. The fluid impermeable barrier 1002 may be similar or identical to the fluid impermeable barrier 102 as disclosed herein, in one or more aspects. For example, the fluid impermeable barrier 1002 may be constructed of any of the materials disclosed herein for the fluid impermeable barrier 102. The fluid impermeable barrier 1002 at least partially defines the chamber 1004. For example, the inner surface 1003 of the fluid impermeable barrier 1002 at least partially defines the perimeter of the chamber 1004. The chamber 1004 may be similar or identical to the chamber 104 in one or more aspects. For example, the chamber 1004 may at least temporarily retain fluids therein. As shown, the fluid collection device 1000 may include the porous material 1015 therein. The porous material 1015 may be similar or identical to the porous material 115 in one or more aspects. For example, the porous material 1015 may include one or more of a fluid permeable membrane 1018 or a fluid permeable support 1020. The fluid impermeable barrier 1002 may also define an opening 1010 extending through the fluid impermeable barrier 1002 that is configured to have a male urethra positioned therethrough.

The sheath 1052 and fluid impermeable barrier 1002 may also include at least one aperture 1062 (e.g., vacuum relief hole) that allows the chamber 1004 to remain substantially at atmospheric pressure. The at least one aperture 1062 may be located at any point on the sheath 1052, such as near or nearer the opening 1056. In some examples (not shown), the aperture 1062 may extend through the cap 1066 or be disposed beneath the cap 1066. In some examples, the fluid collection device 1000 may not include the aperture 1062, such as when a more complete seal as desired for the chamber 1004.

The sheath 1052 also includes at least a portion of the conduit 108 therein, such as at least partially disposed in the chamber 1004. For example, the conduit 108 may extend from the sheath 1052 at the distal region 1044 to a proximal region 1042 at least proximate to the opening 1056. The proximal region 1042 may be disposed near or on the skin around the male urethra (e.g., on the penis or pubic area therearound). Accordingly, when a patient lays on their back, fluid (e.g., urine) may aggregate near the opening 1056 against the skin of the subject. The fluid may be removed from the chamber 1004 via the conduit 108.

In some examples, the fluid impermeable barrier 1002 may be constructed of a material and/or have a thickness that allows the sheath 1052 to collapse when placed under vacuum, such as to remove air around a penis in the fluid collection device 1000 during use. In such examples, the conduit 108 may extend only to or into the distal region 1044 in the chamber 1004 (e.g., not through to the area adjacent the opening). In such examples, urine may be collected and removed from the fluid collection device 1000 at the end nearest the aperture 1062. In such examples, the at least one aperture may be located nearest the opening 1056.

In an example, portions of the chamber 1004 may be substantially empty due to the varying sizes and rigidity of the male penis. However, in some examples, the outermost regions of the chamber 1004 (e.g., periphery of the interior regions of the sheath 1052) may include porous material 1015 (e.g., one or more of the fluid permeable membrane 1018 and fluid permeable support 1020). For example, the porous material 1015 may be bonded to the inner surface 1003 of the fluid impermeable barrier 1002. The porous material 1015 may be positioned (e.g., at the distal end of the chamber 1004) to blunt a stream of urine from the male urethra thereby limiting splashing and/or to direct the fluid(s) to a selected region of the chamber 1004. Since the chamber 1004 is substantially empty (e.g., substantially all of the chamber 1004 forms a reservoir), the fluids are likely to pool at a gravimetrically low point of the chamber 1004. The gravimetrically low point of the chamber 1004 may be at an intersection of the skin of an wearer and the fluid collection device 1000, a corner formed in the sheath 1052, or another suitable location depending on the orientation of the wearer.

The porous material 1015 may include one or more of the fluid permeable membrane 1018 or the fluid permeable support 1020. The fluid permeable membrane 1018 and the fluid permeable support 1020 may be similar or identical to the fluid permeable membrane 118 or the fluid permeable support 120 as respectively disclosed herein, in one or more aspects such as material make-up or wicking ability. One or more of the fluid permeable membrane 1018 or the fluid permeable support 1020 may be disposed between the fluid impermeable barrier 1002 and a penis inserted into the chamber 1004. The fluid permeable membrane 1018 may be positioned between the fluid impermeable barrier 1002 and a penis inserted into the chamber 1004, such as between the fluid permeable support 1020 and penis of a wearer as shown. The fluid permeable support 1020 may be positioned between the fluid permeable membrane 1018 and the fluid impermeable barrier 1002. The inner surface 1003, optionally including the end of the chamber 1004 substantially opposite the opening 1010, may be covered with one or both the fluid permeable membrane 1018 or the fluid permeable support 1020. The fluid permeable support 1020 or the fluid permeable membrane 1018 may be affixed (e.g., adhered) to the fluid impermeable barrier 1002. The fluid permeable support 1020 or the fluid permeable membrane 1018 may be affixed to each other. In some examples, the porous material 1015 only includes the fluid permeable membrane 1018 or the fluid permeable support 1020.

The fluid collection device 1000 includes shape memory material 1030 in one or more portions thereof. The shape memory material 1030 may be similar or identical to any of the shape memory materials disclosed herein, in one or more aspects. For example, the shape memory material 1030 may be composed of the same materials as those disclosed herein for the shape memory material 130. As shown, the shape memory material 1030 may be incorporated into the fluid impermeable barrier 1002, incorporated into the porous material 1015, incorporated into the conduit 108, or may be provided as one or more separate bodies (e.g., is distinct from the other components of the fluid collection device 1000) which are attached to the fluid collection device 1000. The shape memory material 1030 may be incorporated into the fluid impermeable barrier 1002 as disclosed herein with respect to the shape memory material 130 of FIGS. 1A-1C. For example, the fluid impermeable barrier 1002 may be at least partially composed of shape memory material 1030 such as a shape memory polymer.

Figure 10C:
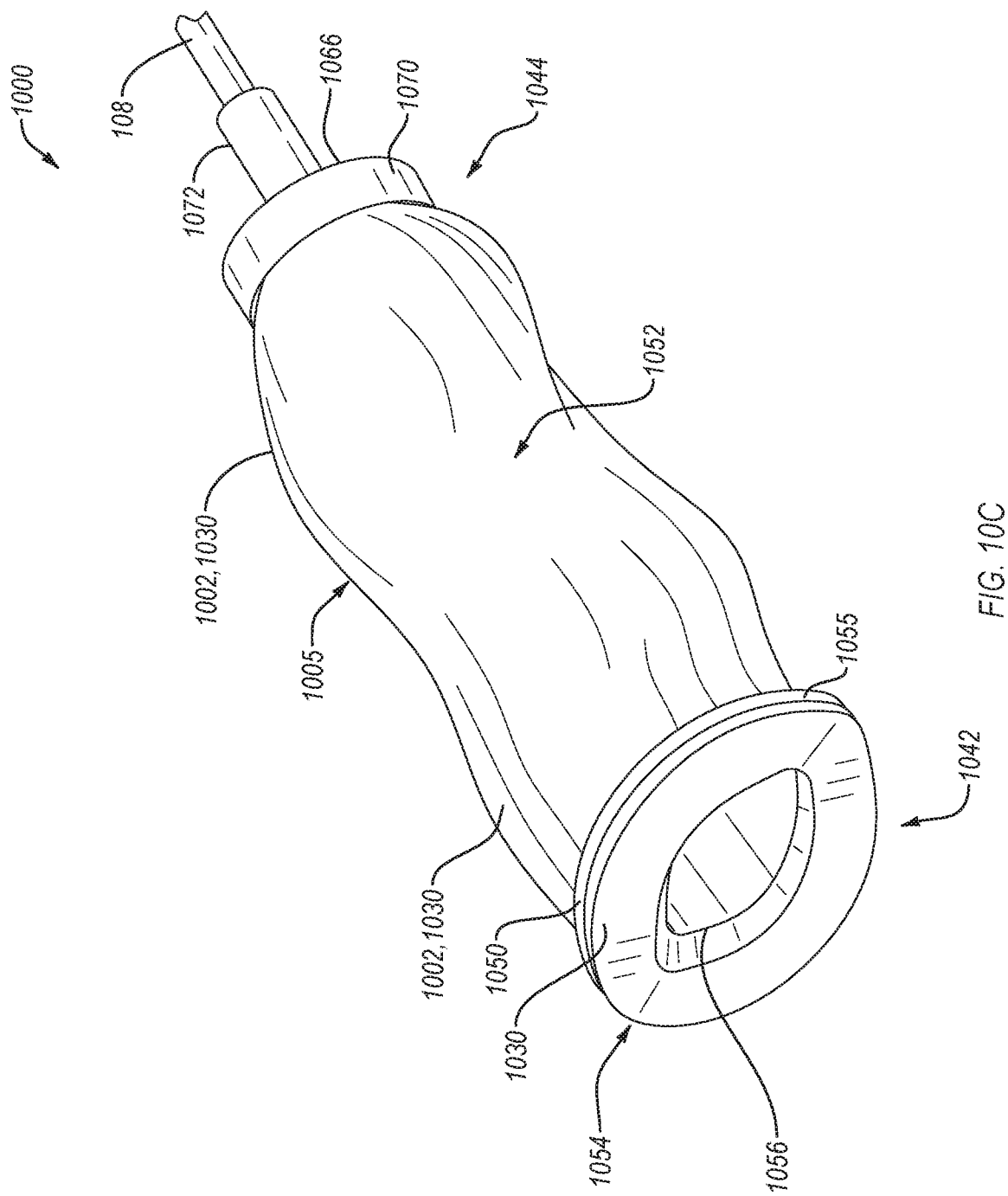
FIG. 10C is an isometric view of the fluid collection device in a second state, according to an embodiment.

As shown in FIGS. 10A-10C, one or more elements of the shape memory material 1030 may be carried by the receptacle 1050, such as attached to a portion of the receptacle 1050 that is expected to be disposed nearest the skin of the wearer when in use. For example, the shape memory material 1030 may include one or more elements disposed on or embedded within the receptacle 1050 (e.g., annular base 1054). In some examples, a laterally extending flange 1055 of the receptacle 1050 may have the shape memory material 1030 attached thereto. The shape memory material 1030 on the receptacle 1050 may be provided in a annular shape that has an outer lateral dimension equal to or less than the outer lateral dimension(s) of the receptacle 1050 and has an opening at least as large as the opening 1056. Accordingly, the shape memory material 1030 may be disposed on or over the penis of a wearer in the same manner as the receptacle 1050, such that the male urethra is positioned in the chamber 1004 when worn.

FIG. 10C is an isometric view of the fluid collection device 1000 in a second state, according to an embodiment. The shape memory material 1030 of the fluid collection device 1000 may be placed in a second state or shape compared to the first state or shape depicted in FIG. 10A. For example, depending upon the size of the wearer, the shape memory material 1030 around the receptacle 1050 may be shaped (e.g., bent) to a second shape, such as to conform to one or more body surfaces of the wearer. In examples, the second shape may be a curve with respect to the longitudinal axis of the fluid collection device 1000 or may be an elliptical or a lenticular shape when viewed perpendicular to the longitudinal axis.

As shown, the sheath 1052 may be placed in a second state (e.g., shape) that is different from the first state, such as being longitudinally collapsed or bent with respect to the longitudinal axis of the fluid collection device 1000 as disclosed with respect to the fluid collection devices of FIGS. 1A-9B. For example, the shape memory material 1030 in the sheath 1052 (e.g., in the fluid impermeable barrier 1002) may be placed in a second shape different than the first shape, such as by an external stimuli (e.g., mechanical force). The shape memory material 1030 in the sheath 1052 may be placed back into the first shape or another shape different than the second shape by exposure to an external stimuli, such as electrical stimulus, a mechanical force, heat, or the like.

Returning to FIGS. 10A and 10B, in some examples, the fluid collection device 1000 includes a cap 1066 at a distal region 1044. The cap 1066 defines an interior channel through which the fluids may be removed from the fluid collection device 1000. The interior channel is in fluid communication with the chamber 1004. The cap 1066 may be disposed over at least a portion of the distal region 1044 of one or more of the fluid impermeable barrier 1002 or the porous material 1015. The cap 1066 may be made of a polymer, rubber, or any other fluid impermeable material. The cap 1066 may be attached to one or more of the fluid impermeable barrier 1002, the porous material 1015, or the conduit 108. The cap 1066 may have a laterally extending flange 1070 and a longitudinally extending flange 1072. The laterally extending flange 1070 may cover at least a portion of the distal region 1044 of the fluid collection device 1000. The longitudinally extending flange 1072 may laterally extend a distance from the sheath 1052. The longitudinally extending flange 1072 is sized and configured to receive and fluidly seal against the conduit 108, such as within the interior channel. The conduit 108 may extend a distance within or through the cap 1066, such as to the porous material 1015, through the porous material 1015, or to a point set-off from the porous material 1015. In the latter example, as depicted in FIG. 10B, the interior channel of the cap 1066 may define a reservoir 1022 therein.

The reservoir 1022 is an unoccupied portion of device such as in the cap 1066 and is void of other material. In some examples, the reservoir 1022 is defined at least partially by the porous material 1015 and the cap 1066. During use, the fluids that are in the chamber 1004 may flow through the porous material 1015 to the reservoir 1022. The reservoir 1022 may store at least some of the fluids therein and/or position the fluids for removal by the conduit 108. In some examples, at least a portion of the porous material 1015 may extend continuously between at least a portion of the opening of the interior channel and chamber 1004 to wick any fluid from the opening directly to the reservoir 1022.

In some examples (not shown), the fluid impermeable barrier 1002 may be disposed on or over the cap 1066, such as enclosing the cap 1066 within the chamber 1004.

In some examples, the sheath 1052 may include at least a portion of the conduit 108 therein, such as at least partially disposed in the chamber 1004. For example, the conduit 108 may extend from the sheath 1052 to a region at least proximate to the opening 1056. The inlet of the conduit 108 may be positioned adjacent to the annular base 1054. The inlet of the conduit 108 may be positioned to be adjacent or proximate to the gravimetrically low point of the chamber 1004, such as adjacent to the annular base 1054. For example, the inlet may be co-extensive with or offset from the opening 1056. In examples, the inlet may be positioned adjacent to the distal region 1044 of the sheath 1052 (e.g., substantially opposite the opening).

The proximal region 1042 may be disposed near or on the skin around the male urethra (e.g., around the penis) and the inlet of the conduit 108 may be positioned in the proximal region 1042. The outlet of the conduit 108 may be directly or indirectly coupled to a vacuum source. Accordingly, fluid may be removed from the proximal region 1042 of the chamber 1004 via the conduit 108.

The receptacle 1050, the sheath 1052, the cap 1066, and the conduit 108 may be attached together using any suitable method. For example, at least two of the receptacle 1050, the sheath 1052, the cap 1066, or the conduit 108 may be attached together using at least one of an interference fit, an adhesive, stitching, welding (e.g., ultrasonic welding), tape, any other suitable method, or combinations thereof.

In some examples (not shown), the fluid collection device 1000 may have a one piece design, with one or more of the sheath 1052, the receptacle 1050, and the cap 1066 being a single, integrally formed piece.

Figure 16:
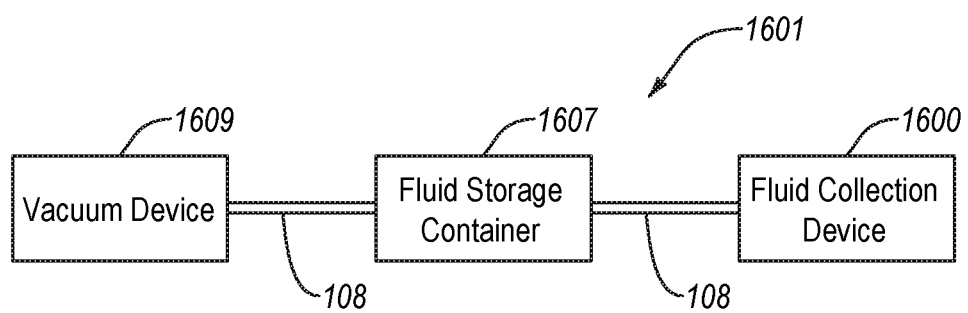
FIG. 16 is a block diagram of a system for fluid collection, according to an embodiment.

Also as shown, the conduit 108 may be at least partially disposed with the chamber of a fluid collection device. The conduit 108 may extend from the distal region 1044 to the proximal region 1042. For example, the conduit 108 may extend through the cap 1066 to a point adjacent to the receptacle 1050. The conduit 108 is sized and positioned to be coupled to a fluid storage container or the vacuum source (FIG. 16). An outlet 112 of the conduit 108 may be operably coupled to the vacuum source, directly or indirectly. The inlet 110 of the conduit 108 may be positioned within the chamber 1004 such as at a location expected to be at the gravimetrically low point of the fluid collection device during use. By positioning the inlet 110 in a location expected to be at the gravimetrically low point of the fluid collection device when worn by the wearer, fluids introduced into the chamber 1004 may be removed via the conduit 108 to prevent pooling or stagnation of the fluid within the chamber 1004.

In some examples, the vacuum source may be remotely located from the fluid collection device 1000. In such examples, the conduit 108 may be fluidly connected to the fluid storage container, which may be disposed between the vacuum source and the fluid collection device 1000.

During operation, a male using the fluid collection device 1000 may discharge fluid(s) (e.g., urine) into the chamber 1004. The fluid(s) may pool or otherwise be collected in the chamber 1004. At least some of the fluid(s) may be pulled through the interior of the conduit 108 via the inlet. The fluid may be drawn out of the fluid collection device 1000 via the vacuum/suction provided by the vacuum source. During operation, the aperture 1062 may substantially maintain the pressure in the chamber 1004 at atmospheric pressure even though fluid is introduced into and subsequently removed from the chamber 1004.

Figure 11:
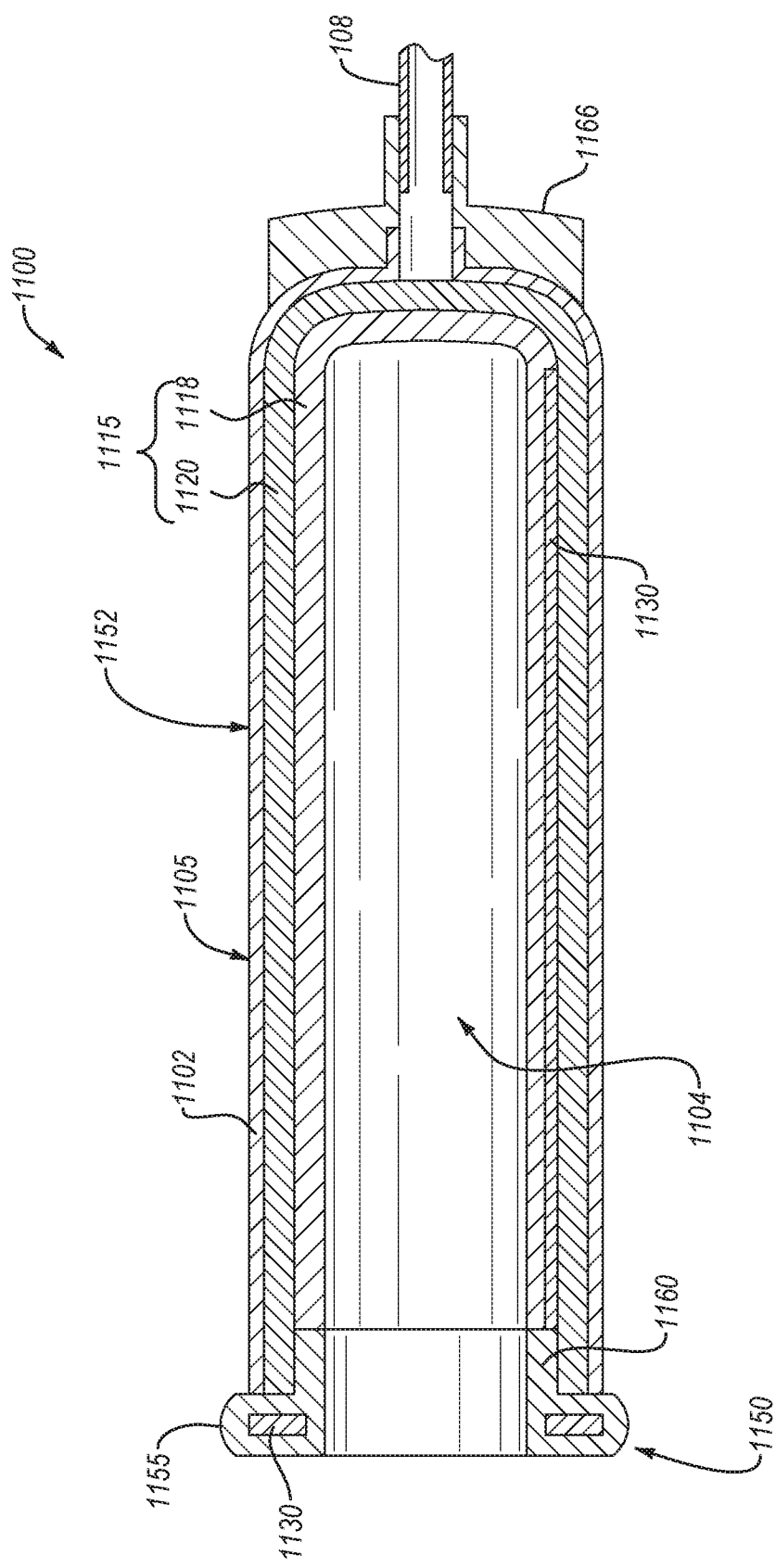
FIG. 11 is a cross-sectional view of a fluid collection device, according to an embodiment.

In some embodiments, the shape memory material may be distinct from the other components of the fluid collection device and/or may be disposed in one or more portions of the fluid collection device different than those depicted in FIGS. 10A-10C. For example, the shape memory material may be located within the receptacle. FIG. 11 is a cross-sectional view of a fluid collection device 1100, according to an embodiment. Except as otherwise disclosed herein, the fluid collection device 1100 is the same or substantially similar to the fluid collection device 1000, in one or more aspects. For example, the fluid collection device 1100 includes one or more of the receptacle 1150, the sheath 1152, the cap 1166, or the conduit 118, as described herein. As shown, the shape memory material 1130 may be carried by the receptacle 1150, such as embedded therein. The laterally extending flange 1155 or the longitudinally extending flange 1160 may include the shape memory material 1130 therein, such as overmolded over the shape memory material 1130. The shape memory material 1130 may be at least partially (e.g., completely) encapsulated within the receptacle 1150. While shown as extending perpendicularly to the longitudinal axis of the fluid collection device 1100 in the laterally extending flange 1155, the shape memory material 1130 may be oriented in a longitudinal direction of the fluid collection device 1100, such as within the longitudinally extending flange 1160. By embedding the shape memory material 1130 within the receptacle 1150, the shape memory material 1130 may not be perceptible on the skin of a wearer.

One or more elements of the shape memory material 1130 may be disposed within the chamber 1104 such as within the porous material 1115. As shown, the shape memory material 1130 may be disposed between the fluid permeable support 1120 and the fluid permeable membrane 1118. By locating the shape memory material 1130 within the porous material 1115, the shape memory material 1130 may not be perceptible (e.g., felt through the materials) from the outer surface 1105 of the fluid permeable membrane 1118 or the chamber 1104.

The shape memory material 1130 may be the same or substantially similar to any of the shape memory materials disclosed herein. For example, the shape memory material 1130 may include one or more of at least one wire, at least one plate, or a plurality of interconnected wires. As such, the shape memory material 1130 may exhibit any of the dimensions disclosed.

The fluid permeable support 1120, the fluid permeable membrane 1118, or the shape memory material 1130 may be affixed (e.g., adhered) to the fluid impermeable barrier 1102. One or more of the fluid permeable support 1120, the fluid permeable membrane 1118, and the shape memory material 1130 may be affixed to each other.

Figure 12:
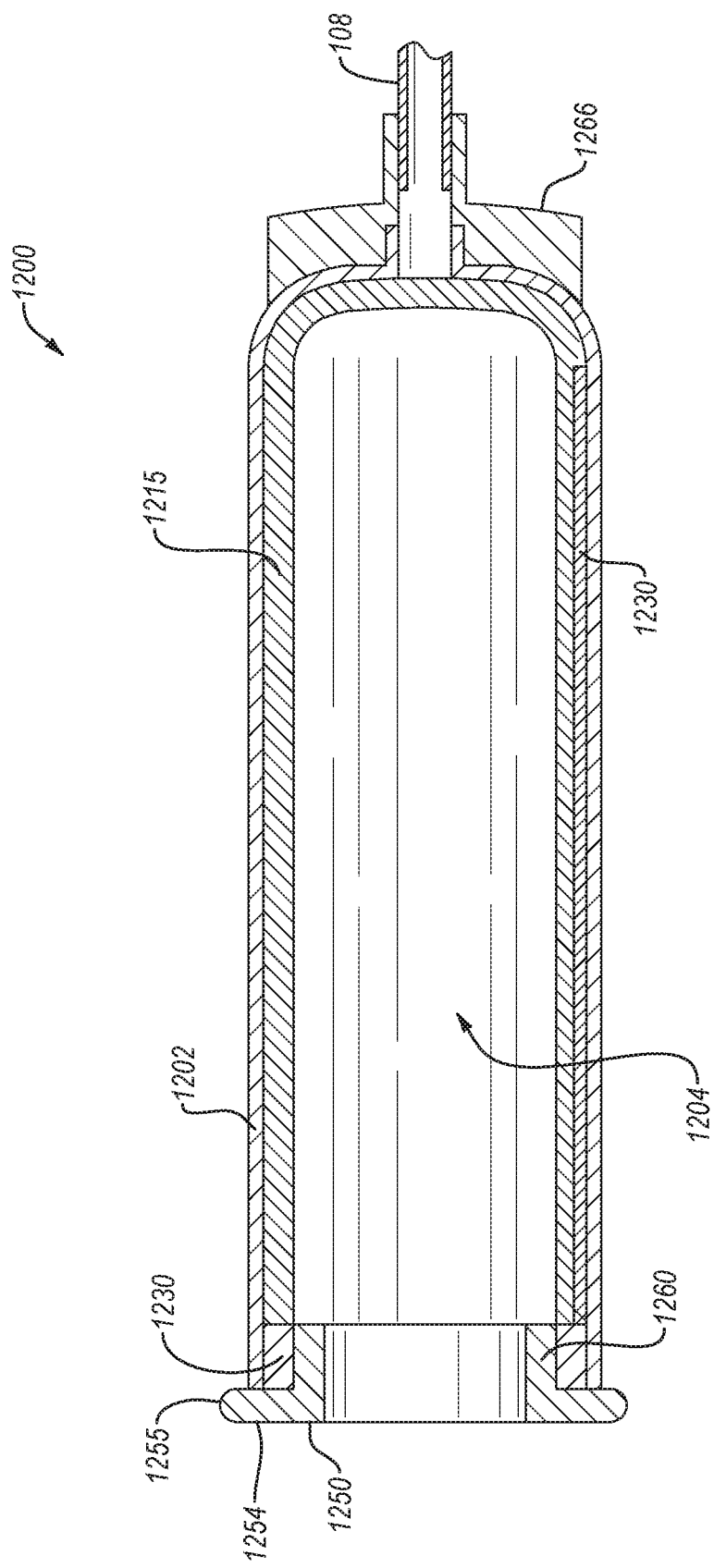
FIG. 12 is a cross-sectional view of a fluid collection device, according to an embodiment.

In some examples, the shape memory material may be located on the receptacle. FIG. 12 is a cross-sectional view of a fluid collection device 1200, according to an embodiment. Except as otherwise disclosed herein, the fluid collection device 1200 is the same or substantially similar to one or more of fluid collection devices 1000 or 1100, in one or more aspects. For example, the fluid collection device 1200 includes one or more of the receptacle 1250, the sheath 1252, the cap 1266, or the conduit 108, as described herein. As shown, one or more elements of the shape memory material 1230 may be carried by the receptacle 1250, such as on an outer surface thereof. One or more of the laterally extending flange 1255 or the longitudinally extending flange 1260 may carry the shape memory material 1230 thereon. The shape memory material 1230 may be disposed at least partially around the longitudinally extending flange 1260 and on the longitudinally extending flange as shown. While shown as extending parallel to the longitudinal axis of the fluid collection device 1200 on the longitudinally extending flange 1260, the shape memory material 1230 may be oriented in a direction perpendicular to the longitudinal axis of the fluid collection device 1200, such as parallel to the laterally extending flange 1260. The porous material 1215 may not extend to the annular base 1254 (e.g., to the laterally extending flange 1255). In such examples, the porous material 1215 may abut or extend from the shape memory material 1230. As shown, the shape memory material 1230 and porous material 1215 may be overcoated or overmolded by the fluid impermeable barrier 1202.

As shown, one or more elements of the shape memory material 1230 may be carried by the sheath 1252, such as between the fluid impermeable barrier 1202 and the porous material 1215 within the chamber 1204. For example, the shape memory material 1230 may be disposed between the fluid impermeable barrier 1202 and one or more of the fluid permeable membrane 1218 or the fluid permeable support 1220. The shape memory material 1230 may be the same or substantially similar to any of the shape memory materials disclosed herein. By disposing one or more elements of the shape memory material 1230 between the fluid impermeable barrier 1202, the porous material 1215, and the receptacle 1250, the shape memory material 1230 may not be perceptible on the skin of the wearer from any of the surfaces of the fluid collection device 1200.

Figure 13:
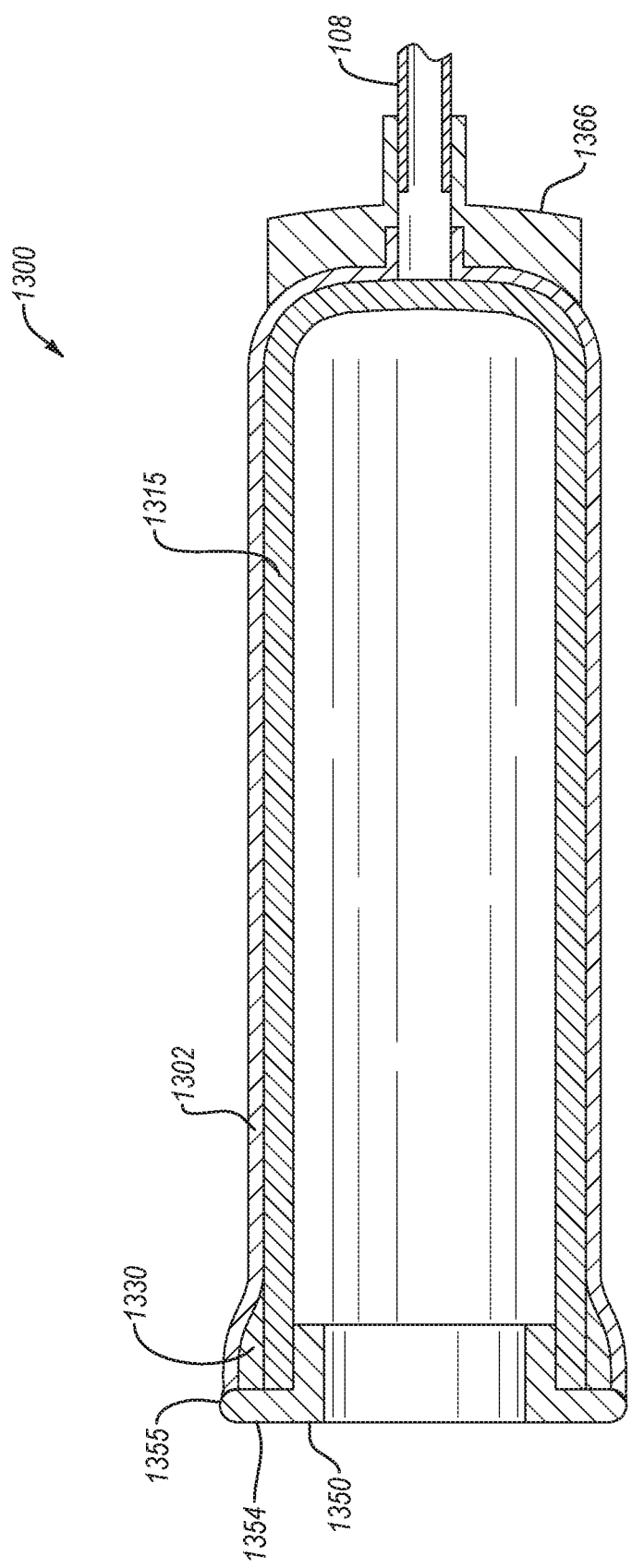
FIG. 13 is a cross-sectional view of a fluid collection device, according to an embodiment.

The shape memory material may be located on the receptacle. FIG. 13 is a cross-sectional view of a fluid collection device 1300, according to an embodiment. Except as otherwise disclosed herein, the fluid collection device 1300 is the same or substantially similar to one or more of fluid collection devices 1000-1200, in one or more aspects. For example, the fluid collection device 1300 includes one or more of the receptacle 1350, the sheath 1352, the cap 1366, or the conduit 108, as described herein. The shape memory material 1330 may be disposed in a discrete portion of the fluid collection device 1300 and at least partially (e.g., completely) encapsulated within materials of the fluid collection device 1300. As shown, the shape memory material 1330 may be disposed between the porous material 1315 and the fluid impermeable barrier 1302. The laterally extending flange 1355 may include the shape memory material 1330 thereon. The fluid impermeable barrier 1302 and the porous material 1315 may extend to the annular base 1354 such as to the laterally extending flange 1355. While shown as extending parallel to the longitudinal axis of the fluid collection device 1300 on the laterally extending flange 1355, the shape memory material 1330 may be oriented perpendicular to the longitudinal axis of the fluid collection device 1300. By embedding the shape memory material 1330 between the fluid impermeable barrier 1302, the porous material 1315, and the annular base, the shape memory material 1330 may not be perceptible on the skin of a wearer.

As shown, the shape memory material 1330 may be shaped to provide a relatively smooth outer surface or inner surface of the fluid collection device 1300. Such selective shapes may provide a relatively smooth outer surface, which prevents discomfort and sores due to discontinuities on the outer surface of the fluid collection device.

Figure 14:
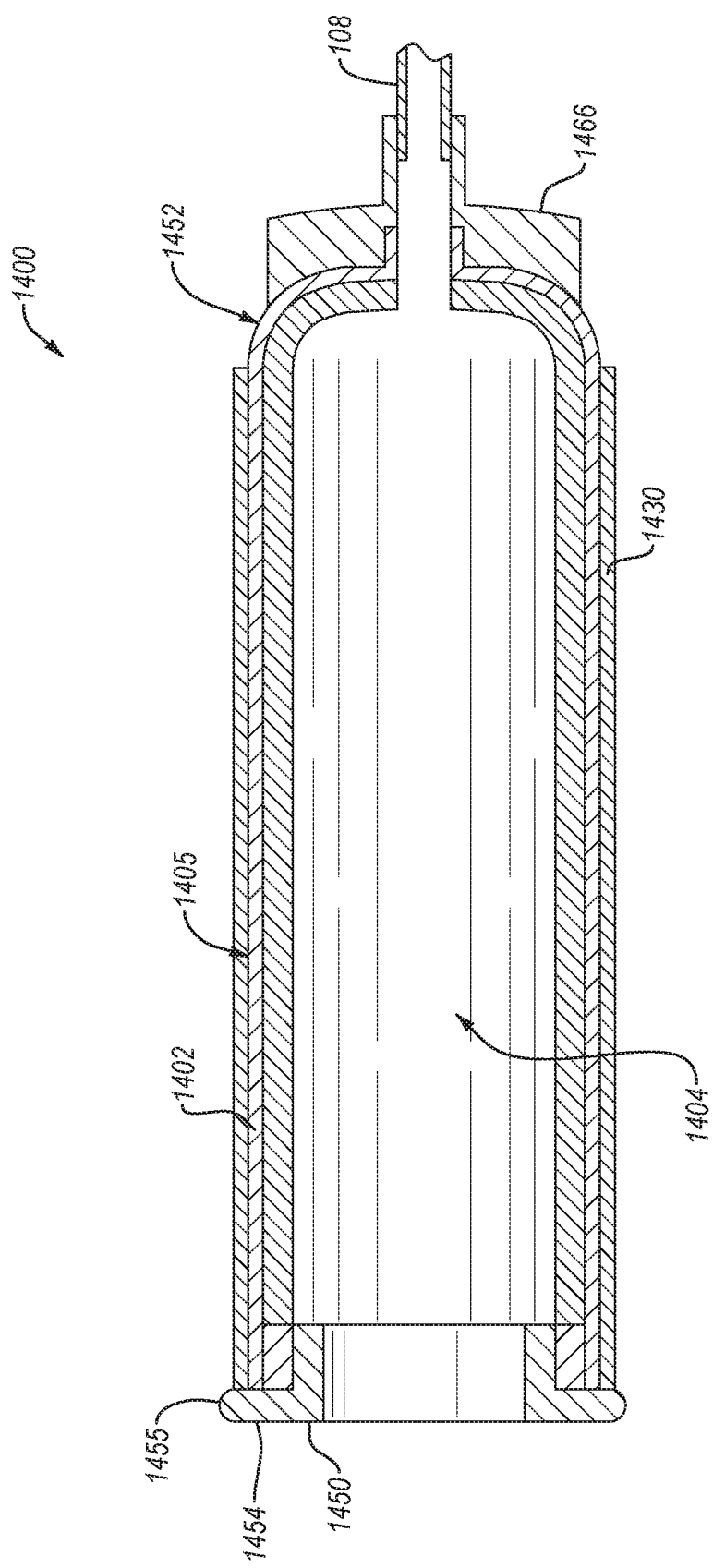
FIG. 14 is a cross-sectional view of a fluid collection device, according to an embodiment.

The shape memory material may be located on the sheath. FIG. 14 is a cross-sectional view of a fluid collection device 1400, according to an embodiment. Except as otherwise disclosed herein, the fluid collection device 1400 is the same or substantially similar to one or more of fluid collection devices 1000-1300, in one or more aspects. For example, the fluid collection device 1400 includes one or more of the receptacle 1450, the sheath 1452, the cap 1466, or the conduit 108, as described herein. The shape memory material 1430 may be disposed on one or more portions of the outer surface 1405 of the fluid collection device 1400. As shown, the shape memory material 1430 may be affixed to the fluid impermeable barrier 1402 such as via an adhesive. The shape memory material 1430 may extend to the receptacle 1450, such as to the annular base 1454. The fluid impermeable barrier 1402 and the porous material 1415 may extend to the annular base 1454 such as to the laterally extending flange 1455. In some examples, the shape memory material 1430 may extend around the entire circumference of at least a portion of the sheath 1452. For example, the shape memory material 1430 may be substantially tubular. By disposing the shape memory material 1430 on the outer surface 1405 of the fluid impermeable barrier 1402, the shape memory material 1430 may not be perceptible to the skin of the wearer from the inside of the chamber 1404.

As shown, the shape memory material 1430 may be shaped to provide a relatively smooth outer surface of the fluid collection device 1400. Such selective a relatively smooth outer surface prevents discomfort and sores due to discontinuities on the outer surface of the fluid collection device. Accordingly, the shape memory material 1430 may be provided with a relatively smooth outer surface. In an embodiment, the shape memory material may be coated in a relatively softer material such as silicone or another polymer to provide a relatively smooth outer surface.

Figure 15:
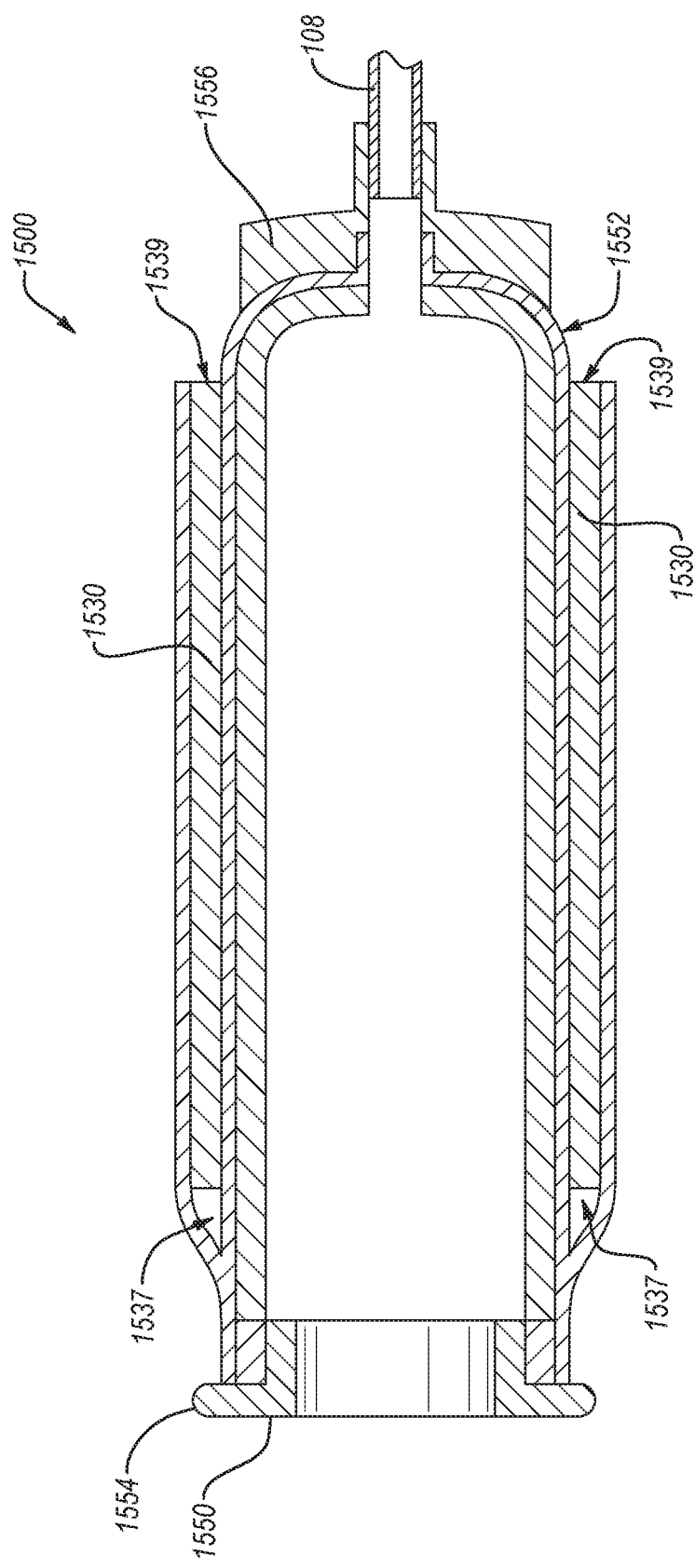
FIG. 15 is a cross-sectional view of a fluid collection device, according to an embodiment.

The shape memory material may be located in a cavity defined by the fluid impermeable barrier. FIG. 15 is a cross-sectional view of a fluid collection device 1500, according to an embodiment. Except as otherwise disclosed herein, the fluid collection device 1500 is the same or substantially similar to one or more of fluid collection devices 1000-1400, in one or more aspects. For example, the fluid collection device 1400 includes one or more of the receptacle 1550, the sheath 1552, the cap 1566, or the conduit 108, as described herein.

The fluid impermeable barrier 1502 defines at least one cavity 1537 that is configured to at least partially receive the shape memory material 1530. The fluid impermeable barrier 1502 may also define at least one aperture 1539 that allows the shape memory material 1530 to be inserted into and/or removed from the cavity 1537. The cavity 1537 and the aperture 1539 may be the same or substantially similar to the cavity 737 and the aperture 739. The cavity may only extend around a portion of the circumference of the sheath 1552 or may extend around the entire circumference of at least a portion of the sheath 1552 (e.g., the cavity 1537 may be substantially tubular). By disposing the shape memory material 1530 in the cavity 1537, the shape memory material 1530 may not be perceptible to the skin of the wearer, the shape memory material 1530 may be replace or reused, or different shape memory materials 1530 may be selected.

It is noted that the receptacle 1550 may also define at least one cavity (not shown) that is configured to receive at least one shape memory material and at least one aperture that allows the shape memory material to be inserted into and/or removed from the cavity of the receptacle 1550.

Additional examples of fluid collection devices that may be used to collect urine from male urethras that may include shape memory materials are disclosed in U.S. patent application Ser. No. 16/433,773 filed on Jun. 7, 2019, the disclosure of which is incorporated herein in its entirety.

FIG. 16 is a block diagram of a system 1601 for fluid collection, according to an embodiment. The system 1601 includes a fluid collection device 1600, a fluid storage container 1607, and a vacuum source 1609. The fluid collection device 1600, the fluid storage container 1607, and the vacuum source 1609 may be fluidly coupled to each other via one or more conduits 108. For example, fluid collection device 1600 may be operably coupled to one or more of the fluid storage container 1607 or the vacuum source 1609 via the conduit 108. Fluid (e.g., urine or other bodily fluids) collected in the fluid collection device 1600 may be removed from the fluid collection device 1600 via the conduit 108 which protrudes into the fluid collection device 1600. For example, an inlet of the conduit 108 may extend into the fluid collection device 1600, such as to a reservoir therein. The outlet of the conduit 108 may extend into the fluid collection device 1600 or the vacuum source 1609. Suction force may be introduced into the chamber of the fluid collection device 1600 via the inlet of the conduit 108 responsive to suction (e.g., vacuum) force applied at the outlet of the conduit 108.

The suction force may be applied to the outlet of the conduit 108 by the vacuum source 1609 either directly or indirectly. The suction force may be applied indirectly via the fluid storage container 1607. For example, the outlet of the conduit 108 may be disposed within the fluid storage container 1607 and an additional conduit 108 may extend from the fluid storage container 1607 to the vacuum source 1609. Accordingly, the vacuum source 1609 may apply suction to the fluid collection device 1600 via the fluid storage container 1607. The suction force may be applied directly via the vacuum source 1609. For example, the outlet of the conduit 108 may be disposed within the vacuum source 1609. An additional conduit 108 may extend from the vacuum source 1609 to a point outside of the fluid collection device 1600, such as to the fluid storage container 1607. In such examples, the vacuum source 1609 may be disposed between the fluid collection device 1600 and the fluid storage container 1607.

The fluid collection device 1600 may be similar or identical to any of the fluid collection devices disclosed herein (e.g., 100 and 300-1500) in one or more aspects. The fluid collection device 1600 may be shaped and sized to be positioned adjacent to a female urethra or have a male urethra positioned therethrough (e.g., receive a penis therein). For example, the fluid collection device 1600 may include a fluid impermeable barrier at least partially defining a chamber (e.g., interior region) of the fluid collection device 1600. The fluid impermeable barrier also defines an opening extending therethrough from the external environment. The opening may be positioned adjacent to a female urethra or have a male urethra positioned therethrough. The fluid collection device 1600 may include a fluid permeable membrane disposed within the fluid impermeable barrier. The fluid collection device 1600 may include porous material disposed in the chamber such as one or more of a fluid permeable support and a fluid permeable membrane. The fluid collection device 1600 includes the shape memory material on or incorporated in one or more components thereof. The shape memory material is sized, shaped, and positioned to retain a selected geometric configuration as disclosed herein. The conduit 108 may extend into the fluid collection device 1600 at a first end (e.g., proximal) region, through one or more of the fluid impermeable barrier, fluid permeable membrane, or the fluid permeable support to a second end (e.g., distal) region of the fluid collection device 1600. The conduit 108 includes an inlet and an outlet, the outlet being fluidly coupled to the fluid storage container and the inlet being positioned in a portion of the chamber selected to be at a gravimetrically low point of the fluid collection device when worn.

The fluid storage container 1607 is sized and shaped to retain a fluid therein. The fluid storage container 1607 may include a bag (e.g., drainage bag), a bottle or cup (e.g., collection jar), or any other enclosed container for storing bodily fluid(s) such as urine. In some examples, the conduit 108 may extend from the fluid collection device 1600 and attach to the fluid storage container 1607 at a first point therein. An additional conduit 108 may attach to the fluid storage container 1607 at a second point thereon and may extend and attach to the vacuum source 1609. Accordingly, a vacuum (e.g., suction) may be drawn through fluid collection device 1600 via the fluid storage container 1607. Fluid, such as urine, may be drained from the fluid collection device 1600 using the vacuum source 1609.

The vacuum source 1609 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 1609 may provide a vacuum or suction to remove fluid from the fluid collection device 1600. In some examples, the vacuum source 1609 may be powered by one or more of a power cord (e.g., connected to a power socket), one or more batteries, or even manual power (e.g., a hand operated vacuum pump). In some examples, the vacuum source 1609 may be sized and shaped to fit outside of, on, or within the fluid collection device 1600. For example, the vacuum source 1609 may include one or more miniaturized pumps or one or more micro pumps. The vacuum sources 1609 disclosed herein may include one or more of a switch, a button, a plug, a remote, or any other device suitable to activate the vacuum source 1609.

FIG. 17 is a flow diagram of a method 1700 to collect fluid, according to an embodiment. The method 1700 of collecting fluid may utilize use any of the fluid collection devices and/or fluid collection systems disclosed herein. The method 1700 may include act 1710, which recites "positioning an opening of a fluid collection device adjacent to a female urethra or around a male urethra, the fluid collection device including: a fluid impermeable barrier at least partially defining a chamber, the fluid impermeable barrier also defining an opening extending therethrough, the opening configured to be positioned adjacent to the female urethra or have the male urethra positioned therethrough; a porous material disposed in the chamber; and a shape memory material incorporated in the fluid collection device, the shape memory material being sized, shaped, and positioned to retain a selected geometric configuration." Act 1710 may be followed by act 1720, which recites "shaping the fluid collection device into the selected geometric configuration, wherein the selected geometric configuration is complementary to contours of anatomy of a wearer in a region proximate to the female urethra or the male urethra of the wearer." Act 1720 may be followed by act 1730, which recites "receiving fluid from the female urethra or the male urethra into a chamber of the fluid collection device."

Acts 1710, 1720, 1730 of the method 1700 are for illustrative purposes. For example, the act 1710, 1720, 1730 of the method 1700 may be performed in different orders, split into multiple acts, modified, supplemented, or combined. In an example, one or more of the acts 1710, 1720, 1730 of the method 1700 may be omitted from the method 1700. Any of the acts 1710, 1720, or 1730 may include using any of the fluid collection devices or systems disclosed herein.

Act 1710 recites "positioning an opening of a fluid collection device adjacent to a female urethra or around a male urethra, the fluid collection device including: a fluid impermeable barrier at least partially defining a chamber, the fluid impermeable barrier also defining an opening extending therethrough, the opening configured to be positioned adjacent to the female urethra or have the male urethra positioned therethrough; a porous material disposed in the chamber; and a shape memory material incorporated in the fluid collection device, the shape memory material being sized, shaped, and positioned to retain a selected geometric configuration." The act 1710 of positioning an opening of a fluid collection device adjacent to a female urethra or around a male urethra may include utilizing any of the fluid collection devices or systems disclosed herein. In some examples, act 1710 may include positioning the opening of a female fluid collection device such that the fluid permeable membrane of the female fluid collection device abuts or is positioned proximate to the female urethra. In some examples, positioning an opening of a fluid collection device adjacent to a female urethra or around a male urethra may include positioning the opening over the female urethra, such as positioning a longitudinally extending opening of the fluid collection device over the female urethra.

In some examples, act 1710 may include positioned a receptacle of a male fluid collection device around (e.g., over) the male urethra such that the male urethra is positioned in the receptacle. In such an example, act 1710 may include positioning a sheath of the male fluid collection device around the male urethra, such that the male urethra (e.g., penis) is positioned through an opening of the sheath and in the chamber of the male fluid collection device. For example, positioning an opening of a fluid collection device adjacent to a female urethra or around a male urethra may include positioning a penis in the chamber.

Act 1720 recites "shaping the fluid collection device into the selected geometric configuration, wherein the selected geometric configuration is complementary to contours of anatomy of a wearer in a region proximate to the female urethra or the male urethra of the wearer." Shaping the fluid collection device into the selected geometric configuration may include forming the fluid collection device into a second geometric configuration (e.g., shape) that is different than a first geometric configuration. Shaping the fluid collection device into the selected geometric configuration may include shaping a female fluid collection device (e.g., 100 and 300-900) to contour to the anatomy around the urethra of a female wearer. In some embodiments, shaping the fluid collection device into the selected geometric configuration includes forming the (e.g., a longitudinal shape of the) fluid collection device into an arcuate shape conforming to the perineal region of the wearer. For example, shaping the fluid collection device into the selected geometric configuration may include forming the fluid collection device into an arcuate shape conforming to the vaginal and perineal region of a wearer. In some embodiments, shaping the fluid collection device into the selected geometric configuration includes flattening or rounding a lateral cross-section of the fluid collection device.

Shaping the fluid collection device into the selected geometric configuration may include shaping a male fluid collection device (e.g., 1000-1500) to contour to the anatomy around the urethra of a male wearer. For example, shaping the fluid collection device into the selected geometric configuration may include forming the at least a portion of the receptacle (e.g., the annular base) into a shape conforming to the anatomy of a penile region or pubic region of a male wearer.

Shaping the fluid collection device into the selected geometric configuration may include manually bending, stretching, compressing, or otherwise manipulating at least one portion of the fluid collection device to the selected geometric configuration. In some embodiments, shaping the fluid collection device into the selected geometric configuration includes flattening or rounding a lateral cross-section of the fluid collection device. In some embodiments, shaping the fluid collection device into the selected geometric configuration includes compressing or bending a the fluid collection device longitudinally. In some embodiments, shaping the fluid collection device into the selected geometric configuration may include shaping the shape memory material before or after inserting the shape memory material into a cavity defined by the fluid impermeable barrier.

Act 1730 recites, "receiving fluid from the female urethra or the male urethra into a chamber of the fluid collection device." In some examples, receiving fluid from the female urethra or the male urethra into a chamber of the fluid collection device includes receiving the fluid through the opening of the fluid collection device. Receiving fluid from the female urethra or the male urethra into a chamber of the fluid collection device may include wicking the fluid(s) away from the opening using porous material, such as via a fluid permeable membrane and a fluid permeable support. In some examples, receiving fluid from the female urethra or the male urethra into a chamber of the fluid collection device may include receiving the fluid(s) into the chamber of the sheath of the male fluid collection device. Receiving fluid from the female urethra or the male urethra into a chamber of the fluid collection device may include flowing the fluid towards a portion of the chamber that is fluidly coupled to an inlet of a conduit in fluid communication a vacuum source. For instance, receiving fluid from the female urethra or the male urethra into a chamber of the fluid collection device may include flowing the fluid(s) to a substantially unoccupied portion of the chamber (e.g., a reservoir), to a gravimetrically low point of the chamber, etc., such as via gravity, wicking, or suction force. In some examples, wicking the fluid into the chamber via the fluid permeable membrane and fluid permeable support may include wicking urine into a reservoir in the fluid collection device.

The method 1700 may include applying suction with a vacuum source effective to suction the fluid(s) from the chamber via a conduit disposed therein and fluidly coupled to the vacuum source may include using any of the vacuum sources disclosed herein. Applying suction with a vacuum source may include activating the vacuum source (e.g., suction device) in fluid communication with the inlet of the conduit in the fluid collection device. In some examples, activating the vacuum source in fluid communication with the inlet of the conduit in the fluid collection device may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the fluid(s) from the chamber via the conduit disposed therein that is fluidly coupled to the vacuum source.

In some examples, applying suction with a vacuum source effective to suction the fluid(s) from the chamber via a conduit disposed therein and fluidly coupled to the vacuum source may be effective to remove at least some fluid (e.g., urine) from the chamber (e.g., interior region) of the fluid collection device. In some examples, applying suction with a vacuum source effective to suction the fluid(s) from the chamber via a conduit disposed therein and fluidly coupled to the vacuum source may be effective to transfer at least some of the fluid from the chamber to a fluid storage container (e.g., a bottle or bag), such as from one or more of a reservoir, fluid permeable support, or fluid permeable membrane.

In some examples, the vacuum source (e.g., suction device) may be disposed on or within the fluid collection device and applying suction with the vacuum source may include activating the vacuum source. In some examples, the vacuum source may be spaced from the fluid collection device and applying suction with the vacuum source may include activating the vacuum source.

In some examples, applying suction with a vacuum source effective to suction the fluid(s) from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of fluid from the chamber of the fluid collection device. In the latter case, a wearer may receive the indication (e.g., from the controller) and activate the vacuum pump manually.

In an example, the method 1500 may include collecting the fluid(s) that are removed from the fluid collection device, such as into a fluid storage container that is spaced from the fluid collection device and fluidly coupled to the conduit. The fluid storage container may include any of the fluid storage containers disclosed herein.

While various aspects and embodiments have been disclosed herein, other aspects and embodiments are contemplated. The various aspects and embodiment disclosed herein are for purposes of illustration and are not intended to be limiting.

What is claimed is:
1. A fluid collection device, comprising:
   a fluid impermeable barrier at least partially defining a chamber, the fluid impermeable barrier also defining an opening extending therethrough, the opening configured to be positioned adjacent to a female urethra or have a male urethra positioned therethrough, the fluid impermeable barrier extending along a longitudinal axis;
   at least one porous material disposed in the chamber;
   at least one shape memory material being sized, shaped, and positioned to retain a selected geometric configuration, the at least one shape memory material exhibiting a length measured along a longitudinal axis of the at least one shape memory material, the length of the at least one shape memory material generally parallel to the longitudinal axis of the fluid impermeable barrier, the length of the at least one shape memory material 30% to 100% of a length of the fluid collection device; and
   at least one cavity that directly receives the at least one shape memory material, the at least one cavity configured to have the at least one shape memory material inserted and/or removed therefrom.
2. The fluid collection device of claim 1, wherein the at least one shape memory material includes a shape memory polymer or a metal.
3. The fluid collection device of claim 1, wherein the at least one shape memory material includes one or more longitudinally extending elements at least one of disposed on or embedded within the fluid impermeable barrier.

4. The fluid collection device of claim 1, wherein the at least one shape memory material includes one or more longitudinally extending elements embedded within the at least one porous material.

5. The fluid collection device of claim 1, wherein the at least one shape memory material is distinct from the fluid impermeable barrier and the at least one porous material.

6. The fluid collection device of claim 5, wherein the at least one shape memory material includes a plurality of interconnected wires.

7. The fluid collection device of claim 1, wherein the fluid impermeable barrier defines at least one recess that at least partially receives the at least one shape memory material.

8. The fluid collection device of claim 7, wherein the fluid impermeable barrier includes at least one protrusion that defines the at least one recess.

9. The fluid collection device of claim 1, wherein the at least one porous material defines at least one recess that at least partially receives the at least one shape memory material.

10. The fluid collection device of claim 1, wherein the fluid impermeable barrier defines a generally cylindrical shape with a longitudinally extending opening therein; and
wherein the at least one shape memory material includes one or more longitudinally extending elements embedded within the at least one porous material along at least a back portion of the fluid impermeable barrier substantially opposite the longitudinally extending opening.

11. The fluid collection device of claim 1, further comprising a conduit including an inlet and an outlet, the inlet being positioned within the fluid collection device and the outlet is configured to be fluidly coupled to a fluid storage container, wherein the at least one shape memory material is at least one of incorporated into the conduit or disposed adjacent to the conduit.

12. The fluid collection device of claim 1, further comprising:
a conduit including an inlet and an outlet, the inlet being positioned within the fluid collection device and the outlet is configured to be fluidly coupled to a fluid storage container; and
at least one brace extending from the conduit to the at least one shape memory material or a portion of the fluid collection device.

13. The fluid collection device of claim 1, wherein:
the fluid impermeable barrier defines a generally tubular shape;
the fluid collection device includes an annular base defining the opening, wherein the annular base is sized and shaped to be positioned around a penis so that the penis is positioned within the chamber; and
the shape memory material includes one or more elements disposed on or embedded within the annular base.

14. A fluid collection system, comprising:
a fluid storage container configured to hold a fluid;
a fluid collection device including: a fluid impermeable barrier at least partially defining a chamber, the fluid impermeable barrier also defining an opening extending therethrough, the opening configured to be positioned adjacent to a female urethra or have a male urethra positioned therethrough, the fluid impermeable barrier extending along a longitudinal axis;
at least one porous material disposed in the chamber;
at least one shape memory material being sized, shaped, and positioned to retain a selected geometric configuration, the at least one shape memory material exhibiting a length measured along a longitudinal axis of the at least one shape memory material, the length of the at least one shape memory material generally parallel to the longitudinal axis of the fluid impermeable barrier, the length of the at least one shape memory material 30% to 100% of a length of the fluid collection device; and
at least one cavity that directly receives the at least one shape memory material, the at least one cavity configured to have the at least one shape memory material inserted and/or removed therefrom and
a vacuum source fluidly coupled to one or more of the fluid storage container or the fluid collection device via the conduit, the vacuum source configured to draw fluid from the fluid collection device via the conduit.

15. A method to collect fluid, the method comprising:
positioning an opening of a fluid collection device adjacent to a female urethra or around a male urethra, the fluid collection device including:
a fluid impermeable barrier at least partially defining a chamber, the fluid impermeable barrier also defining an opening extending therethrough, the opening configured to be positioned adjacent to the female urethra or have the male urethra positioned therethrough, the fluid impermeable barrier extending along a longitudinal axis;
at least one porous material disposed in the chamber;
at least one shape memory material being sized, shaped, and positioned to retain a selected geometric configuration, the at least one shape memory material exhibiting a length measured along a longitudinal axis of the at least one shape memory material, the length of the at least one shape memory material generally parallel to the longitudinal axis of the fluid impermeable barrier, the length of the at least one shape memory material 30% to 100% of a length of the fluid collection device; and
at least one cavity that directly receives the at least one shape memory material, the at least one cavity configured to have the at least one shape memory material inserted and/or removed therefrom
shaping the fluid collection device into the selected geometric configuration, wherein the selected geometric configuration is complementary to contours of anatomy of a wearer in a region proximate to the female urethra or the male urethra of the wearer; and
receiving fluid from the female urethra or the male urethra into a chamber of the fluid collection device.

16. The method of claim 15, wherein positioning an opening of a fluid collection device adjacent to a female urethra or around a male urethra includes positioning the opening over the female urethra.

17. The method of 15, wherein positioning an opening of a fluid collection device adjacent to a female urethra or around a male urethra includes positioning a penis in the chamber.

18. The method of claim 15, wherein shaping the fluid collection device into the selected geometric configuration includes forming the fluid collection device into an arcuate shape conforming to a vaginal and perineal region of a wearer.

19. The method of claim 15:
further comprising at least one of inserting the at least one shape memory material into the at least one cavity or removing the at least one shape memory material from the cavity.

20. The fluid collection device of claim 1, wherein the cavity exhibits a cross-sectional shape and size that is larger than a cross-sectional shape and size of the at least one shape memory material.

21. The fluid collection device of claim 1, wherein the at least one cavity includes at least one aperture configured to receive the at least one shape memory material, and further comprising a device that switches the at least one aperture from an open state that allows the at least one shape memory material to be inserted and removed from the at least one cavity and a closed state that inhibits the at least one shape memory material from being inserted and removed from the at least one cavity.

22. The fluid collection device of claim 1, wherein the at least one cavity is distinct from and spaced from the chamber or encompass only a portion of the chamber.

23. The fluid collection device of claim 1, wherein the at least shape memory material is at least partially disposed in the at least one porous material.

24. The fluid collection device of claim 1, further comprising a conduit extending through the at least one porous material, wherein the at least shape memory material is coupled to the conduit.

* * * * *